(12) United States Patent
Jean et al.

(10) Patent No.: US 11,642,444 B2
(45) Date of Patent: May 9, 2023

(54) INTERFACE DEVICE BETWEEN AN EXTERNAL EQUIPMENT AND LINES INTENDED TO BE CONNECTED TO A PATIENT SYSTEM

(71) Applicant: UBIPLUG, Saint Contest (FR)

(72) Inventors: Eric Jean, Bieville-Beuville (FR); Fabrice Missaire, Lillois (BE); Sylvain Thuaudet, Fresne-Camilly (FR)

(73) Assignee: UBIPLUG, Saint Contest (FR)

( * ) Notice: Subject to any disclaimer, the term of this patent is extended or adjusted under 35 U.S.C. 154(b) by 0 days.

(21) Appl. No.: 17/785,270

(22) PCT Filed: Dec. 9, 2020

(86) PCT No.: PCT/EP2020/085364
§ 371 (c)(1),
(2) Date: Jun. 14, 2022

(87) PCT Pub. No.: WO2021/122242
PCT Pub. Date: Jun. 24, 2021

(65) Prior Publication Data
US 2023/0050010 A1    Feb. 16, 2023

(30) Foreign Application Priority Data
Dec. 15, 2019    (FR) ........................ 1914441

(51) Int. Cl.
*A61M 1/36*    (2006.01)
*A61M 1/26*    (2006.01)
(Continued)

(52) U.S. Cl.
CPC ........ *A61M 1/152* (2022.05); *A61M 39/1011* (2013.01)

(58) Field of Classification Search
CPC ..................... A61M 1/152; A61M 39/1011
See application file for complete search history.

(56) References Cited

U.S. PATENT DOCUMENTS

| 5,713,850 A | 2/1998 | Heilmann et al. |
| 5,894,011 A | 4/1999 | Prosl et al. |
(Continued)

FOREIGN PATENT DOCUMENTS

| EP | 3 643 342 A1 | 4/2020 |
| WO | 2005/046439 A2 | 5/2005 |
| WO | 2009/001152 A1 | 12/2008 |

OTHER PUBLICATIONS

International Search Report of PCT/EP2020/085364 dated Mar. 10, 2021 [PCT/ISA/210].
(Continued)

*Primary Examiner* — Dirk R Bass
(74) *Attorney, Agent, or Firm* — Sughrue Mion, PLLC

(57) ABSTRACT

An interface device between external equipment and at least a venous tube for transferring fluid to a patient, the interface device having at least a first port adapted to be connected to an outlet port of the external equipment; and a venous port carried by a stator of the interface device in order to inject the fluid into the venous tube. The interface device includes a third port, the first port and the third port being carried by a movable assembly that is movable relative to the stator, the interface device being arranged to pass from any one of its configurations to another one of its configurations by the movable assembly moving relative to the stator.

21 Claims, 13 Drawing Sheets

(51) Int. Cl.
    *A61M 39/22*     (2006.01)
    *A61M 1/14*     (2006.01)
    *A61M 39/10*     (2006.01)

(56) References Cited

U.S. PATENT DOCUMENTS

| | | |
|---|---|---|
| 6,596,234 B1 | 7/2003 | Schnell et al. |
| 2005/0145549 A1 | 7/2005 | Jonsson et al. |

OTHER PUBLICATIONS

Written Opinion of PCT/EP2020/085364 dated Mar. 10, 2021 [PCT/ISA/237].

Stp 5
P5
Venous restitution

Stp 4
P6
Dialysis

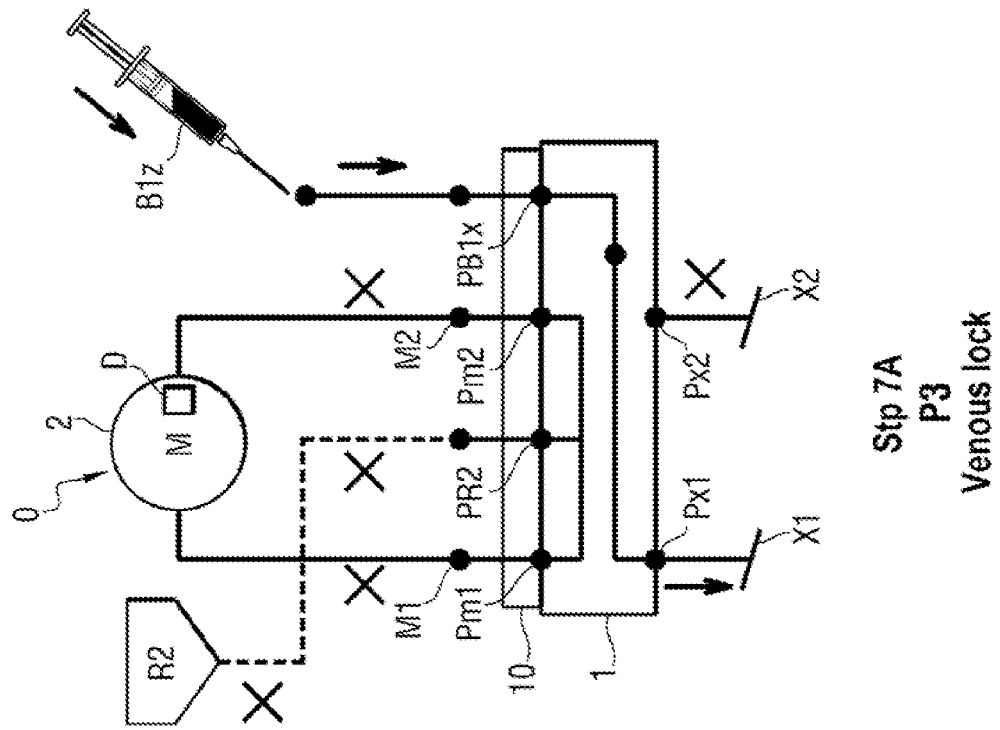
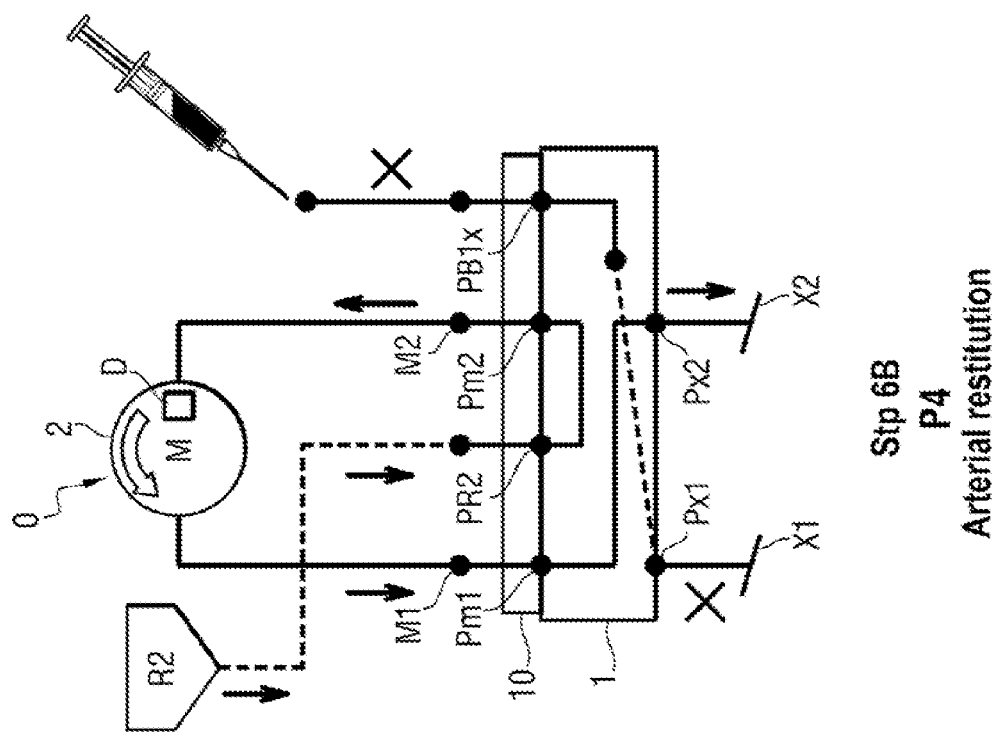

Stp 0
P1
Disconnection

Stp 7B
P2
Arterial lock

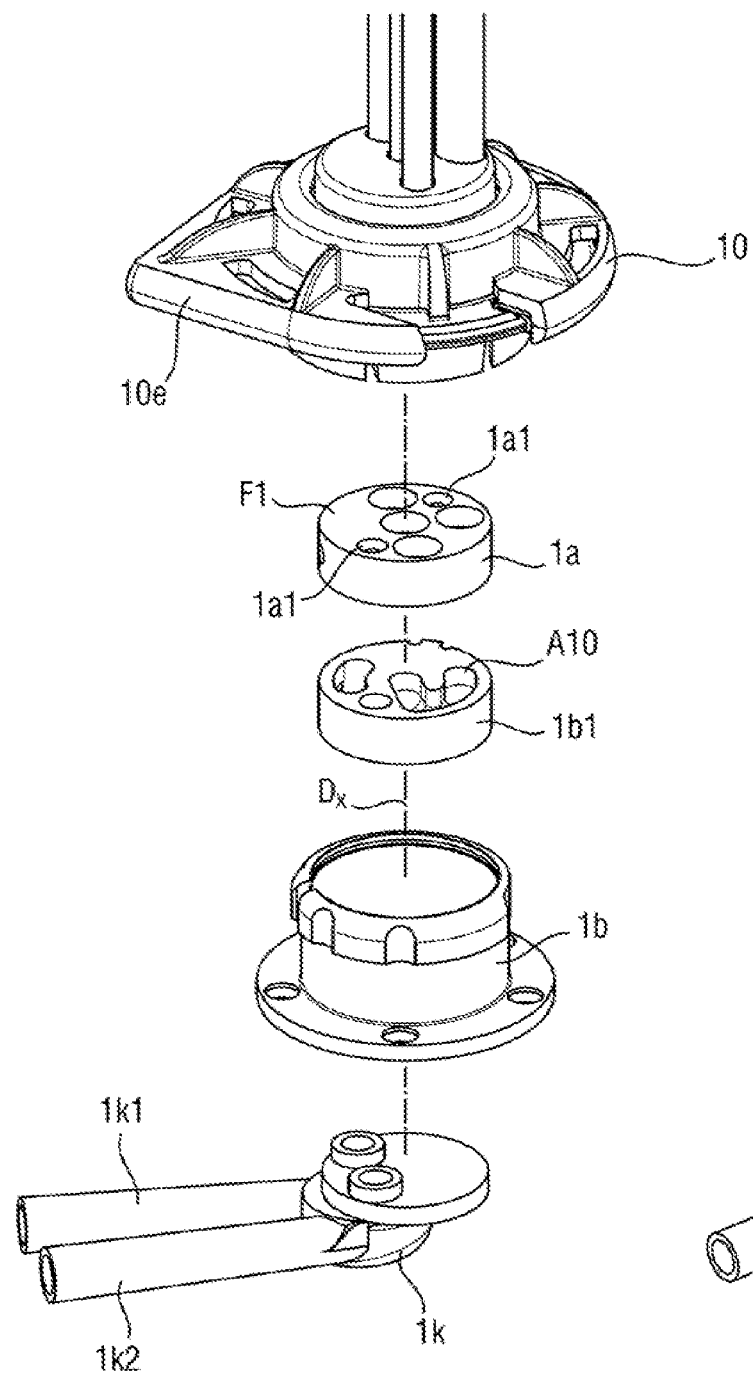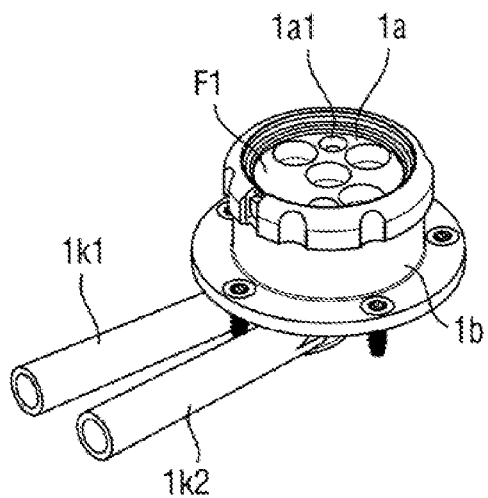
Fig. 6
Fig. 7

INTERFACE DEVICE BETWEEN AN EXTERNAL EQUIPMENT AND LINES INTENDED TO BE CONNECTED TO A PATIENT SYSTEM

CROSS REFERENCE TO RELATED APPLICATIONS

This application is a National Stage of International Application No. PCT/EP2020/085364 filed on Dec. 9, 2020, claiming priority based on French Patent Application No. 1914441 filed on Dec. 15, 2019.

DESCRIPTION

The invention relates to the field interface devices between firstly external equipment such as a hemodialysis machine, a supply of nutritional fluid, or a supply of medicinal fluid, and secondly at least one tube that is to be connected to a patient system, such as the circulatory system or the digestive system.

BACKGROUND OF THE INVENTION

Certain pathologies require fluid to be injected into a patient system.

Implanting the tube(s) used for performing an injection is traumatic for the patient.

Thus, when a series of injections needs to be performed over a period of several days or several weeks or several months, it is preferred to leave the tube(s) connected with the patient system so that they can be reused for a plurality of successive injections.

The connection between the external equipment and the patient is then made via at least one venous tube and via an interface device that serves as a connector between the external equipment and the tube that leads into the patient's system.

Between two injections, the tube(s) remaining implanted in the patient need to be maintained in an environment that limits any risk of pathogenic elements developing.

To do this, after the injection has been performed, a locking fluid is injected into each tube.

The locking fluid serves to avoid clogging of the tube(s) that lead into the patient system and to avoid needing to replace tubes or catheters.

The particular circumstance of hemodialysis is described below.

Hemodialysis consists in causing a patient's blood to flow into external equipment of the hemodialysis machine type, and then after the blood has been treated by the hemodialysis machine, restituting the blood to the patient's circulatory system.

In order to provide the connection between the dialysis machine and the patient's circulatory system, medical staff connect a first duct to the hemodialysis machine and cause a liquid to flow in the first duct in order to expel gas therefrom.

Once the first duct has been purged of its gas, it is connected mechanically via an interface device to said at least one tube/catheter that has previously been implanted in the patient (each tube/catheter leading into the patient's circulatory system).

It is then possible to begin sucking blood towards the hemodialysis machine.

At the end of a hemodialysis session, the catheter attached to the patient is disconnected from the machine and physiological serum is injected into it in order both to restitute the blood that is to be found in the catheter to the patient's circulatory system and also to rinse the tube.

Finally, each at least one tube is connected to locking fluid injection means, and the locking fluid is injected into each tube/catheter.

Between two hemodialysis sessions, the locking fluid present in each tube/catheter serves to limit any risk of pathogens/infection developing via the tube.

The locking fluid is removed when it is desired to perform a new hemodialysis.

All those manual operations are repeated each time it is desired to connect the patient to the hemodialysis machine via a catheter. Thus, when both a venous catheter and an arterial catheter are implanted to admit blood into the patient and to take blood from the patient, even more manual operations need to be performed. This leads to an increased risk of the patient's circulatory system being contaminated.

An interface device for performing hemodialysis is described in patent document U.S. Pat. No 5,713,850A.

That device serves to exchange fluid with the patient via a single tube attached to the patient.

Consequently, both for injecting a nutritional fluid into a patient system (the digestive system or the circulatory system, as appropriate) and also for injecting a medicinal fluid or a dialysis fluid into the circulatory system, it would be useful to develop an interface device that minimizes any risk of contaminating the patient system.

OBJECT OF THE INVENTION

An object of the present invention is to provide an interface device between external equipment and at least a venous tube, the device resolving the above-mentioned drawbacks of the prior art, in full or in part.

SUMMARY OF THE INVENTION

To this end, the invention provides an interface device between external equipment and at least a venous tube for connecting to a patient system in order to transfer fluid from the equipment to the patient system, the interface device comprising at least:
  a first port adapted to be connected to an outlet port of the external equipment; and
  a venous port for injecting the fluid into the venous tube;
  the interface device being adapted to adopt selectively a first configuration in which fluid is prevented from passing between the first port and the venous port and a second configuration in which the first port is connected to the venous port to allow fluid to pass from the first port to the venous port.

The interface device of the invention is essentially characterized:
  firstly in that it includes a third port and in that it is adapted to adopt selectively a venous lock access configuration that is different from said first and second configurations, the third port being connected in this venous lock access configuration to the venous port while the first port is isolated from the venous port; and
  secondly in that the venous port is carried by a stator of the interface device, the first port and the third port being carried by a movable assembly of the interface device that is movable relative to the stator, the interface device being arranged to pass from any one of its configurations to another one of its configurations by the movable assembly moving relative to the stator.

Having at least first and third ports carried by a movable assembly of the device (the movable assembly is preferably a rotor) and having at least one venous port carried by the stator of the device serves to facilitate use of the interface device:

since firstly, the ports for connection to the external equipment are carried by a movable assembly that groups them together, while at least said venous port for connection to the patient via the venous tube is carried by the stator; and since secondly, it is the movement of the movable assembly relative to the stator that serves to cause the interface device to pass from any of its selective configurations to another selective configuration.

By using the interface device of the invention, it is no longer necessary to perform the following in succession:

manually connecting a locking liquid suction port forming part of the external equipment with the venous tube (in order to withdraw the locking fluid contained in the venous tube); then manually disconnecting this suction port so as to enable the venous tube to be manually connected to an outlet port of the external equipment (in order to inject fluid from the external equipment into the venous tube); then manually disconnecting this outlet port of the external equipment to enable the venous tube to be manually connected to a port for injecting locking liquid into the venous tube.

By reducing the number of manual operations for connecting and disconnecting ports with the venous tube, the risk of handling errors is greatly reduced, as is the associated risk of contaminating the patient.

The interface device of the invention may be used for:

forming an interface between the venous tube an external equipment of the nutritional fluid supply type, the venous tube then leading into the patient's circulatory or digestive system in order to inject a nutritional fluid solution therein; or forming an interface between the venous tube and external equipment of the medicinal fluid supply type, the venous tube then leading into the patient's circulatory system in order to inject a medicinal fluid solution therein; or forming an interface between the venous tube and external equipment including a hemodialysis machine, the venous tube then leading into the patient's circulatory system in order to exchange blood between the hemodialysis machine and the patient's circulatory system.

In a particular embodiment, the interface device of the invention also comprises a second port that is preferably adapted to be connected to an inlet port of the external equipment (specifically to the inlet port of a hemodialysis machine when the external equipment is a hemodialysis machine), the second port being carried by said movable assembly of the interface device and wherein, in said venous lock access configuration, the first port and the second port (Pm2) are both isolated from the venous port.

In a particular embodiment of the interface device of the invention, the movable assembly is a rotor mounted to turn relative to said stator.

By mounting the movable assembly to turn relative to the stator, it is easy to determine operational clearances between the functional surfaces of the rotor and of the stator as required for providing sealing while allowing the rotor and the stator to move relative to each other.

The movable assembly may also have a face that is visible from the outside of the interface device, and each of the ports carried by the movable assembly opens out in said face.

Since these ports of the movable assembly are grouped together and accessible from a single face, that facilitates connecting them with the ports of the external equipment.

Preferably, the face of the movable assembly and the ports carried by that movable assembly are located completely inside a recess of the stator.

Thus, this face and the ports of the movable assembly are protected in the recess of the stator.

Preferably, the ports carried by the movable assembly are female ports that all open out in a direction that is common to these female ports.

Thus, each of the connections with these female ports is established merely by moving along said common direction Dx.

In a particular embodiment, the interface device of the invention is also adapted to form an interface between the external equipment, which comprises a hemodialysis machine, and an arterial tube for connecting to said patient system in order to transfer fluid from the patient system and to the hemodialysis machine, the interface device further comprising:

a second port adapted to be connected to an inlet port of the hemodialysis machine, the second port being carried by said movable assembly of the interface device;

an arterial port carried by the stator in order to receive fluid from the patient coming from the arterial tube (specifically the fluid is the patient's blood);

the interface device further being adapted to prevent fluid from passing between the second port and the arterial port when the device is in its first configuration and to allow fluid to pass between the second port and the arterial port when the device is in its second configuration.

The interface device enables venous and arterial tubes to be connected to the same hemodialysis machine while making it possible, using the single interface device, either:

simultaneously to prevent fluid from passing between the hemodialysis machine and the venous tube and between the hemodialysis machine and the arterial tube by placing the interface device in its first configuration; or else simultaneously to allow fluid to pass between the hemodialysis machine and the venous tube and between the hemodialysis machine and the arterial tube by placing the interface device in its second configuration.

It is thus possible, with the same interface device, to act selectively to allow or to prevent a fluid flow connection with a vein and with an artery.

This greatly facilitates the manipulations to be performed by medical staff while reducing any risk of manipulation errors.

In order to understand the present invention, and unless specified to the contrary, any port of the interface device that is not explicitly mentioned as being connected to another port of the interface device should be considered as being isolated from all of the other ports of the interface device.

Furthermore, when it is stated that given ports are connected to one another, that means that there is fluid flow communication between those given ports.

Likewise, when it is stated that two given ports are isolated from each other, that means that there is no fluid flow communication between those given ports.

The fluid passing through the interface device is a liquid. For example, the fluid may be blood, a dialyzate, physiological serum, a medicinal fluid (medication in liquid form), a nutritional fluid (a nutritional solution).

In another aspect, the invention provides an interface assembly comprising an interface device in accordance with any of the embodiments of the invention and interface connection means comprising a plug and a plurality of flexible tubes, each having one end connected to the plug and another end carrying at least one connection coupling (each tube having at least one coupling specific thereto), each given connection coupling being for establishing a fluid flow connection between the flexible tube carrying the given connection coupling and a corresponding one of said ports of the external equipment, the plug being arranged to be mechanically connected in releasable manner to said interface device in such a manner that when the plug is mechanically connected to said interface device, each of the flexible tubes of the plurality of flexible tubes is in fluid flow connection with only with that one of the ports carried by said movable assembly that corresponds thereto.

This aspect of the invention is particularly advantageous since it enables a single plug having a plurality of ports to be used for connecting all of the ports of external equipment to all of the ports carried by the movable assembly of the interface device.

This facilitates connecting together the external equipment and the interface device, since the operator does not need to connect each port of the external equipment directly to the corresponding port of the interface device, with the interface connection means with its flexible tubes forming a kind of octopus provided with couplings that are independent of one another and thus easier to manipulate.

Once the ports of the external equipment are connected to the respective couplings of the interface connection means, the operator needs only to connect the plug presenting multiple ports with the interface device on the patient side.

By facilitating these operations, the risk of connecting errors is reduced and it is possible to save operator time.

The interface connection means preferably include a cap arranged to be removably mounted on the plug of the interface connection means, the cap defining a sealed internal volume between the plug and the cap so that each of the flexible tubes connected to the plug can be put into fluid flow connection with the other flexible tubes via this internal volume of the cap.

Thus, before connecting the plug of the interface connection means to said interface device, it is easy to discharge the gas contained in the flexible tubes by causing the liquid to flow through all of the tubes while they are connected to one another via the internal volume of the cap.

This contributes to reducing the time needed for establishing a reliable fluid flow connection between the external equipment and the patient system.

In another aspect, the invention provides a hemodialysis system comprising an interface assembly in accordance with any of the embodiments of the invention and external equipment that comprises a hemodialysis machine.

In the hemodialysis system, the first port of the interface device is releasably connected to the outlet port of the hemodialysis machine via the interface connection means and the second port of the interface device is releasably connected to the inlet port of the hemodialysis machine via the interface connection means.

The hemodialysis machine includes a pump arranged to cause fluid to flow from its inlet port to its outlet port, and the hemodialysis machine also includes a venous tube and an arterial tube.

The venous tube is connected to the venous port of the interface device. In this example, the venous tube is for connecting to a patient's circulatory system in order to transfer blood via the interface device and via the interface connection means from the hemodialysis machine to the circulatory system.

The arterial tube is connected to the arterial port of the interface device. In this example, the arterial tube is for connecting to said patient's circulatory system in order to transfer blood via the interface device and via the interface connection means from the circulatory system to the hemodialysis machine.

The hemodialysis system of the invention is advantageous, at least for the reasons set out above with reference to the interface device of the invention. Finally, in another aspect, the invention provides interface connection means for connecting external equipment to an interface device in order to inject fluid into a patient, the connection means being characterized in that they comprise a plug and a plurality of flexible tubes, each having one end connected to the plug and another end carrying at least one connection coupling, each given connection coupling being for putting the flexible tube carrying the given connection coupling into fluid flow connection with a corresponding port of the external equipment that corresponds to the given connection coupling, the plug having a plurality of male ports, each opening out in a face of the plug, and each of the flexible tubes being in fluid flow connection with a single corresponding one of said male ports, and conversely, each of said male ports being connected to a single corresponding one of said flexible tubes.

The connector means serve to group together a plurality of male ports on a common face of the plug in order to enable these male ports to be put simultaneously into fluid flow connection with corresponding ports formed in an interface device.

BRIEF DESCRIPTION OF THE DRAWINGS

Other characteristics and advantages of the invention appear clearly from the following description given by way of nonlimiting indication and with reference to the accompanying drawings, in which:

FIGS. 1b, 1c, 1d, 1e, 1f, 1g, 1h, 1i, and 1j show respective successive different steps Stp1, Stp3a, Stp3b, Stp4, Stp5, Stp6B, Stp7A, Stp7B, and Stp0 in the operation of an interface device 1 of the invention that is adapted to hemodialysis;

FIG. 6 shows a second exploded view of the FIG. 5 interface assembly 100;

FIG. 7 shows an interface device of the invention adapted to be fastened on a bone of the patient;

DETAILED DESCRIPTION OF THE INVENTION

Figure 1A:
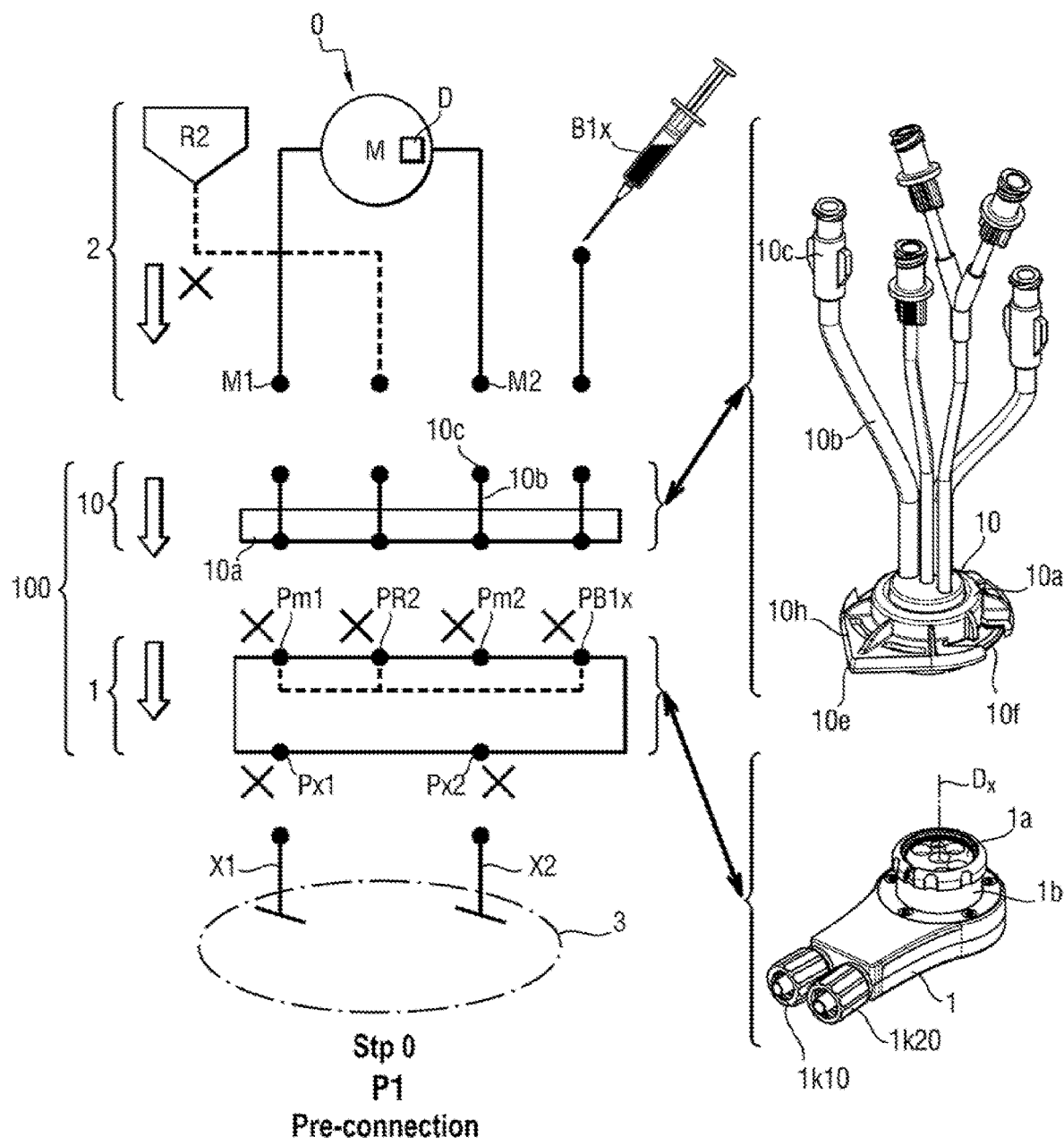
FIG. 1a shows a hemodialysis system 0 of the invention comprising a hemodialysis machine 2, an interface device 1 of the invention, interface connection means 10 of the invention (the interface device 1 and the interface connection means 10 forming an interface assembly 100 of the invention) and venous and arterial tubes X1 and X2, the interface device 1, the venous and arterial tubes X1 and X2, the inlet and outlet ports M1 and M2 of the machine, and the interface connection means are shown in this figure prior to being assembled together for transferring fluid between the external equipment 2 and the patient system 3.

The invention relates mainly to a hemodialysis system 0 as shown in FIGS. 1a to 1j.

The system 0 comprises venous and arterial tubes X1 and X2, together with external equipment 2 that comprises a hemodialysis machine 2 and an interface assembly 100 of the invention.

The interface assembly 100 comprises an interface device 1 of the invention together with interface connection means 10 of the invention.

The interface device of the invention is designed firstly to enable it to be fastened in fluid flow connection with the tubes X1 and X2, and secondly to enable the connection means 10 to be connected directly to the interface device in order to be able to set up fluid flow connections between the external equipment 2 and the patient's circulatory system 3 via the connection means 10 and the interface device 10, which are thus in series between the patient and the external equipment.

Each of the tubes X1 and X2 is arranged to be put into fluid flow communication with the circulatory system 3 of a patient. These venous and arterial tubes X1 and X2 preferably form parts of a single catheter.

Each of the tubes X1 and X2 is preferably formed in a flexible duct, e.g. made of a thermoplastic that is compatible with medical use (polyurethane, PEEK, silicone, etc.), in order to make it easier to handle and route between the circulatory system 3 and the interface device 1.

The venous tube X1 is essentially for injecting fluid from the machine 2 into the patient, and the arterial tube X2 is essentially for taking (sucking) fluid from the patient for delivery to the hemodialysis machine 2.

The tubes are put into connection with the circulatory system 3 either via an arteriovenous fistula, or via a central catheter tunneled in the patient (a tunneled central catheter is a catheter that remains in place in the patient's body between two hemodialyses), or else via an implanted non-tunneled hemodialysis catheter (it being possible for these tubes to form parts of one or more catheters).

More precisely, the interface device 1 of the invention forms:

an interface between external equipment, in this example the hemodialysis machine 2, and an arterial tube X2 for being connected to said circulatory system 3 of the patient in order to transfer fluid and/or blood from the system 3 to the hemodialysis machine 2; and an interface between the hemodialysis machine 2 and at least a venous tube X1 to transfer fluid and/or blood from the hemodialysis machine to the circulatory system 3.

The interface device 1 comprises:

a first port Pm1 adapted to be connected, preferably removably via a first coupling, to an outlet port M1 of the hemodialysis machine 2; and a second port Pm2 adapted to be connected, preferably releasably via a second coupling possibly secured to said first coupling, to an inlet port M2 of the hemodialysis machine;

a venous port Px1 for injecting blood to the venous tube X1, the venous port Px1 preferably being releasably attached via a coupling to the venous tube X1; and an arterial port Px2 for receiving blood from the patient (i.e. causing blood to circulate, e.g. taken by suction), the blood coming from the arterial tube X2, which arterial port Px2 is preferably releasably attached via a coupling to the arterial tube X2.

The second port Pm2 of the interface device 1 is adapted to transfer blood from the interface device 1 to an inlet port M2 of the hemodialysis machine 2.

The hemodialysis machine includes a pump M arranged to pump/circulate fluid from its inlet port M2 to its outlet port M1.

The first port Pm1 of the interface device 1 is adapted to receive blood coming from the outlet port M1 in order to transfer it to the venous tube X1.

The hemodialysis machine 2 is also adapted to perform exchanges between the fluid it is transferring, specifically the patient's blood) and a liquid dialyzate in order to purify the fluid (blood). For this purpose, the hemodialysis machine has an internal circuit connected at one end to the inlet port M2 and at the other end to the outlet port M1.

The pump M of the hemodialysis machine is preferably a peristaltic pump for transferring fluid from the inlet port M2 to the outlet port M1 at an accurately controlled flow rate.

The internal circuit of the hemodialysis machine preferably includes at least one semipermeable membrane allowing exchanges between the fluid/blood and the chemically formulated dialyzate and/or filters for purifying the fluid/blood.

Preferably, the semipermeable membrane allows exchanges between the circuit through which the patient's blood flows and a dialyzate circuit that is not shown. The dialyzate circuit extends from a supply of previously formulated dialyzate to a store for used dialyzate, passing via a zone that is in contact with the semipermeable membrane in order to perform exchanges with the patient's blood.

The hemodialysis machine 2 also has a debubbler D for removing gas bubbles that are contained in the fluid being transferred through the hemodialysis machine 2. In this example, the debubbler D is connected in series between the inlet and outlet ports M2 and M1, and it is preferably located between the port M2 and the membrane. If necessary, the machine may include other debubblers for ensuring that no liquid containing bubbles is delivered to the patient.

The hemodialysis machine may also include respective detector devices for detecting bubbles and/or impurities and/or fluid flow rate between its inlet and outlet ports M2 and M1 and/or fluid pressure passing through the machine 2 and/or the level of dialyzate in a dialyzate supply connected to the machine 2 for bringing the dialyzate into contact with the semipermeable membrane.

The detector device(s) is/are connected to an electronic control unit (not shown) of the hemodialysis machine 2 for controlling the operation of the pump M as a function of the measurements taken thereby.

The electronic unit may also be connected to at least some of said sensors of the dialyzate circuit and to actuators of the dialyzate circuit, e.g. in order to control dialyzate flow rates through the dialyzate circuit, and/or dialyzate dosages with other components.

This electronic unit can also be connected to one or more state sensors for sensing the state of the semipermeable membrane in order to control the operating parameters of various actuators, including the pump M, as a function of the measurements taken using such state sensor(s).

The hemodialysis machine may also include a communication interface (not shown) adapted to detect the current configuration of the interface device 1 of the invention so as to adjust the operation of the hemodialysis machine as a function of the current configuration is detected in this way. This communication interface may comprise electronic connection means connecting the hemodialysis machine 2 to the interface device 1 in detachable manner.

The communication interface may be adapted to transmit:
from the interface device 1 to the hemodialysis machine 2, a current-configuration signal of the interface device 1 representative of the current configuration being adopted by the interface device 1; and/or
from the hemodialysis machine 2 to the interface device 1, a change-of-configuration signal, the interface device 1 including an actuator, e.g. a motor, for controlling the change of configuration of the interface device 1 as a function of the change-of-configuration signal received by the interface device 1 so as to cause the interface device to pass from its current configuration to another configuration selected from a succession of predefined configurations. The various configurations selectively adopted by the interface device are described below.

FIGS. 1a to 1j, 8, and 9 illustrate a succession of configurations that can be selectively adopted by the interface device (the term "selectively" is used to mean that, at any given instant, the interface device can adopt only one configuration from among the listed configurations).

The interface device 1 has a third port PB1x and it is adapted to adopt selectively a venous lock access configuration P3; Stp3b that is distinct from said first and second configurations P1 and P6 that are adopted respectively in steps Stp1 and Stp4.

In this venous lock access configuration P3 (step Stp3b) the third port Pb1x is connected to the venous port Px1 while the first port Pm1 and the second port Pm2 are both isolated from the venous port Px1.

As can be understood from FIGS. 4 to 8, the venous port Px1 is carried by a stator 1b of the interface device 1, while the first port Pm1 and the third port PB1x are carried by a movable assembly 1a, which in this example is a rotor 1a mounted to turn relative to the stator 1b.

This movable assembly 1a is movable relative to the stator 1b over a range that may optionally be limited by abutments.

The interface device 1 is arranged to pass from one of its configurations to another of its configurations by the movable assembly 1a moving relative to the stator 1b.

More particularly, the movable assembly 1a has a face F1 that is visible from the outside of the interface device 1, and each of the ports carried by the movable assembly 1a opens out in said face.

The fluid flow connection between a port carried by the rotor 1a and a port carried by the stator 1b presents the interest of having only one friction zone between the stator and the movable assembly over the path of the fluid flow connection.

This is advantageous since it makes it possible to simplify the design of the device by minimizing the number of dynamic sealing points that need to be developed over the fluid flow path between a port carried by the movable assembly 1a and a port carried by the stator. This serves to minimize the risk of having matter-retention zones over the respective paths between the ports of the movable assembly and the ports of the stator 1b.

This design also makes it possible for the device to be made compact since a plurality of ports can be carried by a single movable part.

Preferably, the face (F1) of the movable assembly (1a) and the ports carried by that movable assembly are located completely inside a recess of the stator.

The ports carried by the movable assembly 1a are preferably female ports that all open out in a direction Dx that is common to these female ports.

This makes it possible both for the movable part 1a to be made compact, while also giving access to the female ports by means of a single movement in translation along the direction Dx.

Each given configuration of the device is thus defined by a given position of the movable part 1a relative to the stator 1b.

Figure 1B:
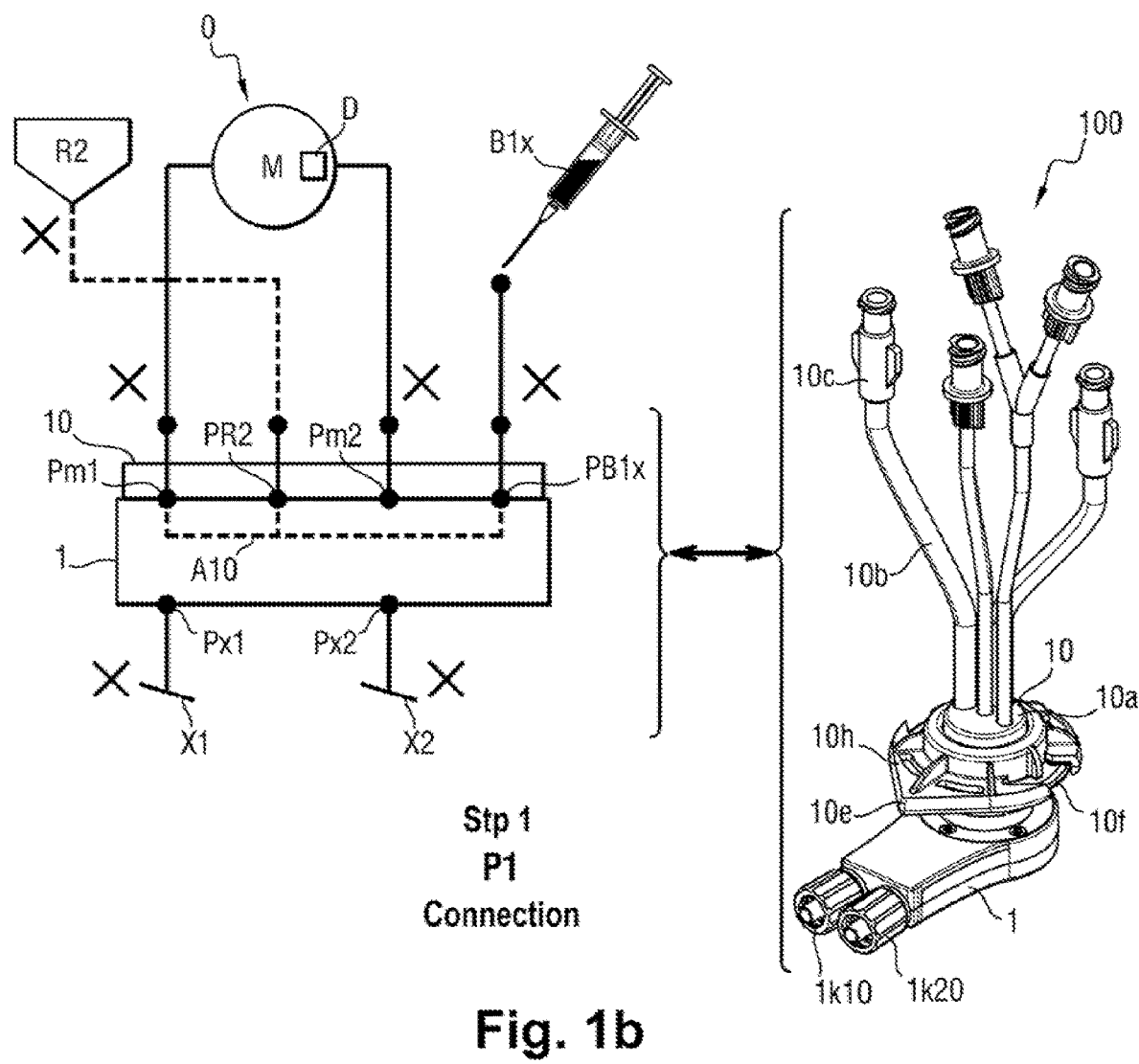
FIG. 1b shows all of the elements of FIG. 1a, but connected together for transferring fluid between the external equipment 2 and the patient system 3, the interface device being shown in its first configuration P1, Stp1 in which the venous ports Px1 and the arterial ports Px2 are closed (in this example the interface device 1 is provided with an external shell since it is to be implanted extracorporeally and not to be fastened on a bone of the patient)
Figure 1D:
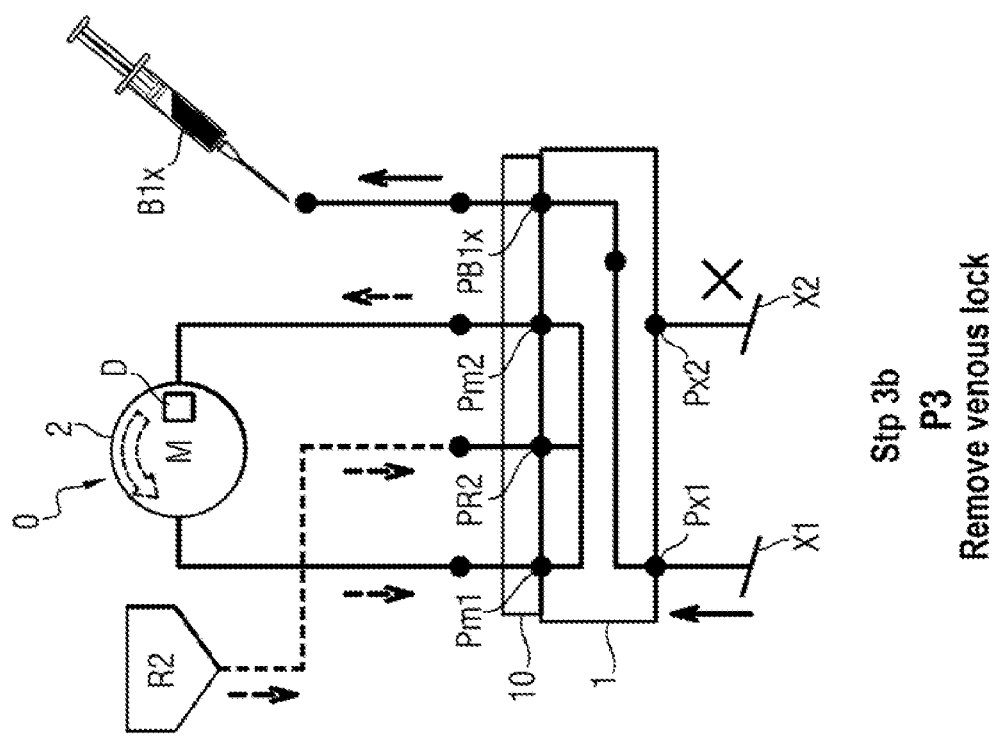
Figure 1C:
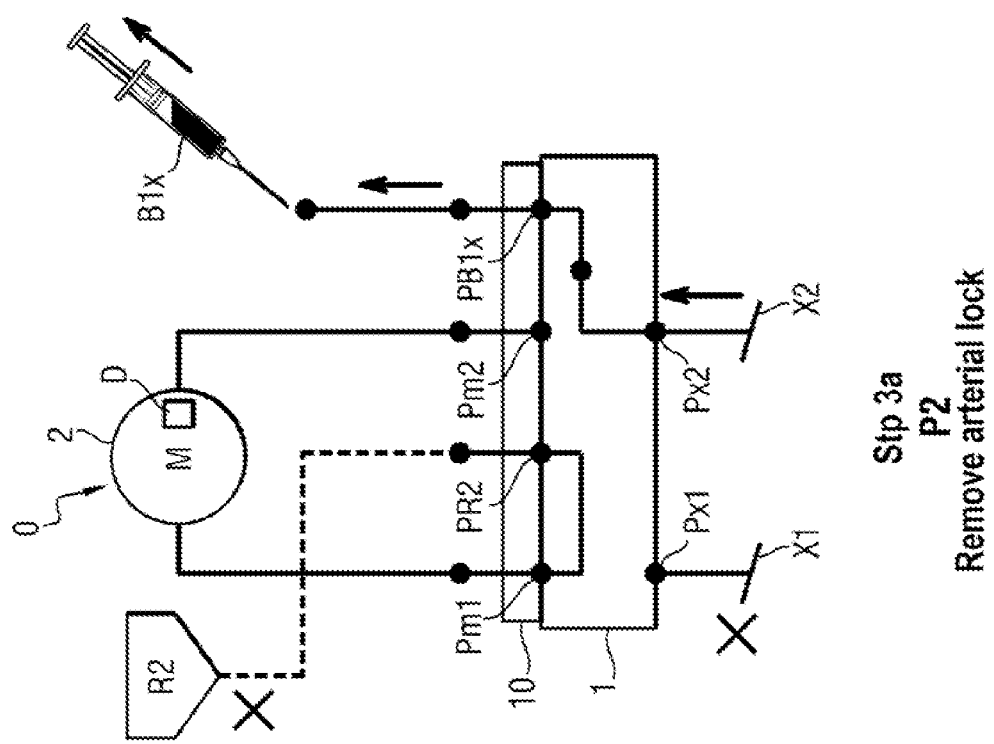
Figure 1F:
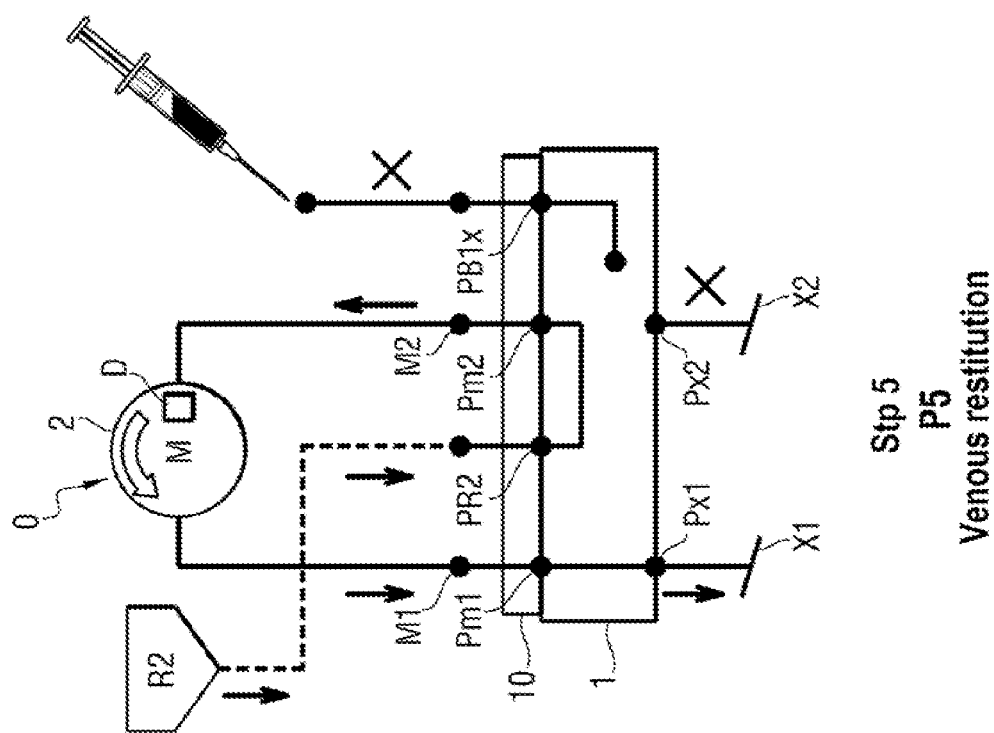
Figure 1E:
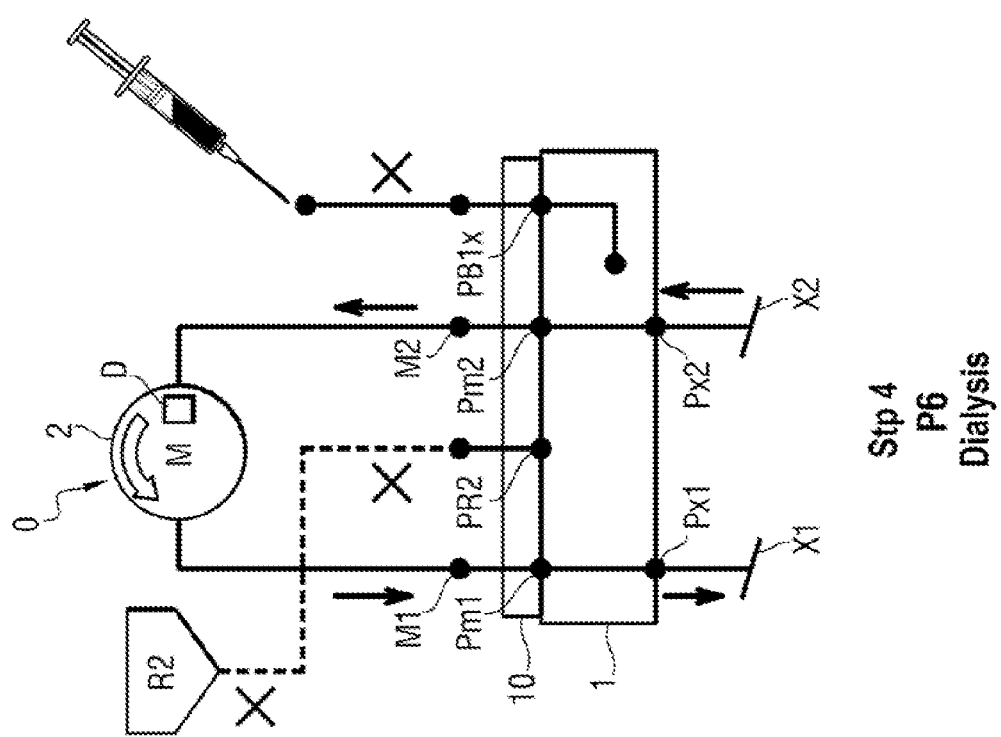
Figure 8:
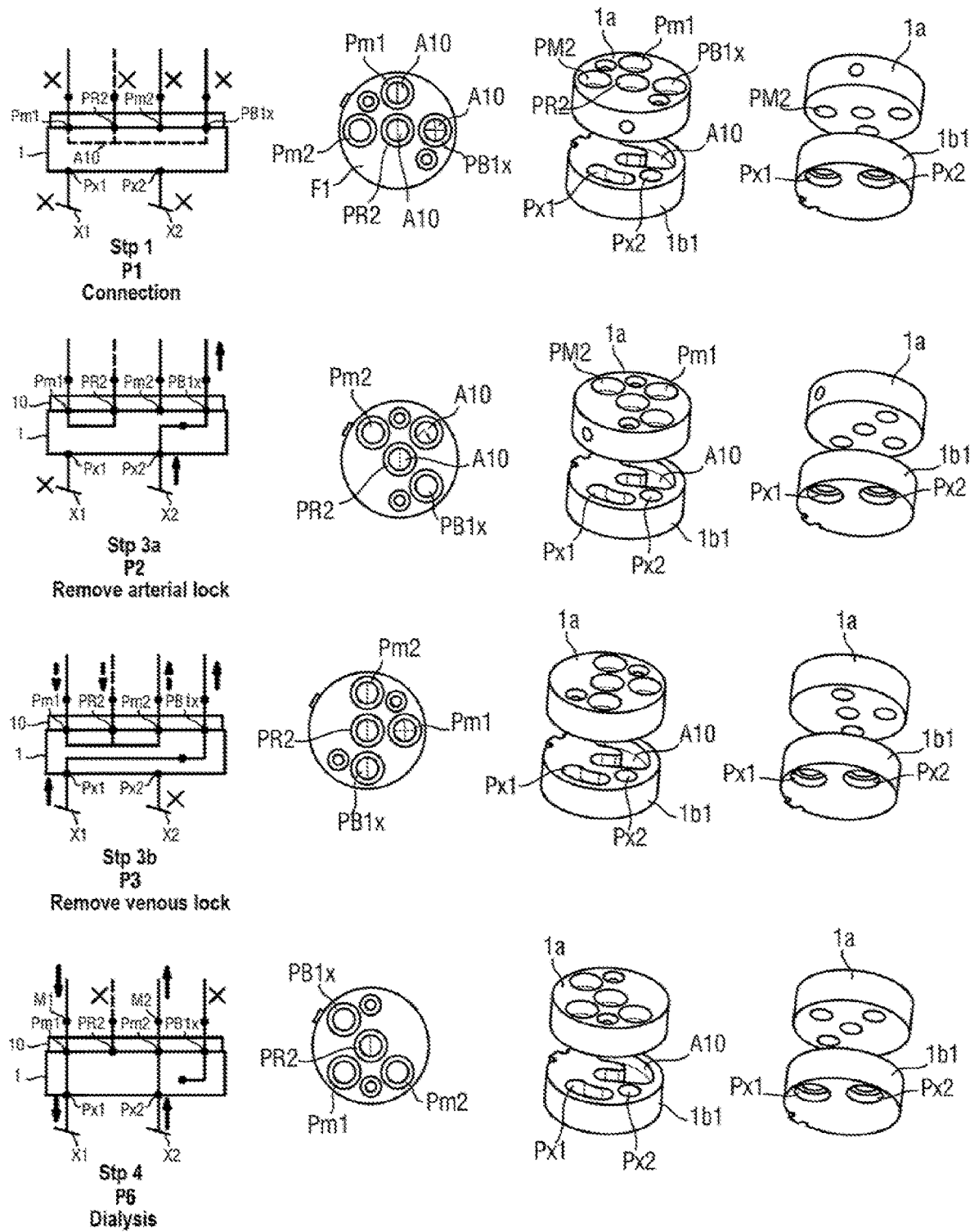
FIG. 8 shows an interface device 1 of the invention in a plurality of successive configurations, specifically the first configuration P1 (adopted in step Stp1), the arterial lock access configuration P2 (adopted in step Stp3a to remove the arterial lock contained in the arterial tube X2), the venous lock access configuration P3 (adopted in step Stp3b to remove the venous lock contained in the venous tube X1), and the second configuration P6 adopted in step Stp4 to perform dialysis)

As can be understood from FIGS. 1a, 1e, and 8, the interface device 1 is adapted to adopt selectively:
- a first configuration P1 that is adopted in the pre-connection step Stp0, the connection step Stp1, and the disconnection step; and
- a second configuration P6 that is adopted during the dialysis step Stp4.

In its first configuration P1:
- blood is prevented from passing between the first port Pm1 and the venous port Px1; and
- blood is prevented from passing between the second port Pm2 and the arterial port Px2.

This first configuration is useful at least for isolating the machine 2 from the patient's circulatory system. In its second configuration P6 (the dialysis step Stp4 shown in FIG 1e), the first port Pm1 is connected to the venous port Px1 to allow blood to pass from the first port Pm1 to the venous port Px1, the second port Pm2 and the arterial port Px2 are also connected together to allow blood to pass from the arterial port Px2 to the second port Pm2. In this second configuration P6, only the ports Pm1, Px1, Pm2, and Px2 are open, and the other ports of the device are closed.

This second configuration P6 is useful for causing blood to flow in a loop passing in succession via the circulatory system 3, the arterial tube X2, the arterial port Px2, the second port Pm2, the inlet port M2, the hemodialysis machine 2 together with its internal circuit, the outlet port M1, the second port Pm1, the venous port Px1, the venous tube X1, and finally the circulatory system 3.

One of the advantages of the interface device 1 of the invention is that it makes it possible, merely by moving the rotor 1a, to go from one configuration to another without needing to disconnect any port from the machine manually.

It is thus possible to allow or to prevent the passage of fluid between the tubes X1, X2, and the hemodialysis machine, while limiting any risk of contaminating the patient.

In a preferred embodiment, the interface device may be arranged so that when it is in its first configuration P1, the first port Pm1 and at least one of the other ports PR2, PB1x carried by the movable assembly 1a are then put into communication via an internal circuit A10 of the interface device 1.

Also in this mode, when the interface device 1 is in its second configuration P6, communication between the first port Pm1 and the other ports (PR2, PB1x, Pm2) carried by the movable assembly (1a) via the internal circuit A10 is then prevented.

Figure 9:
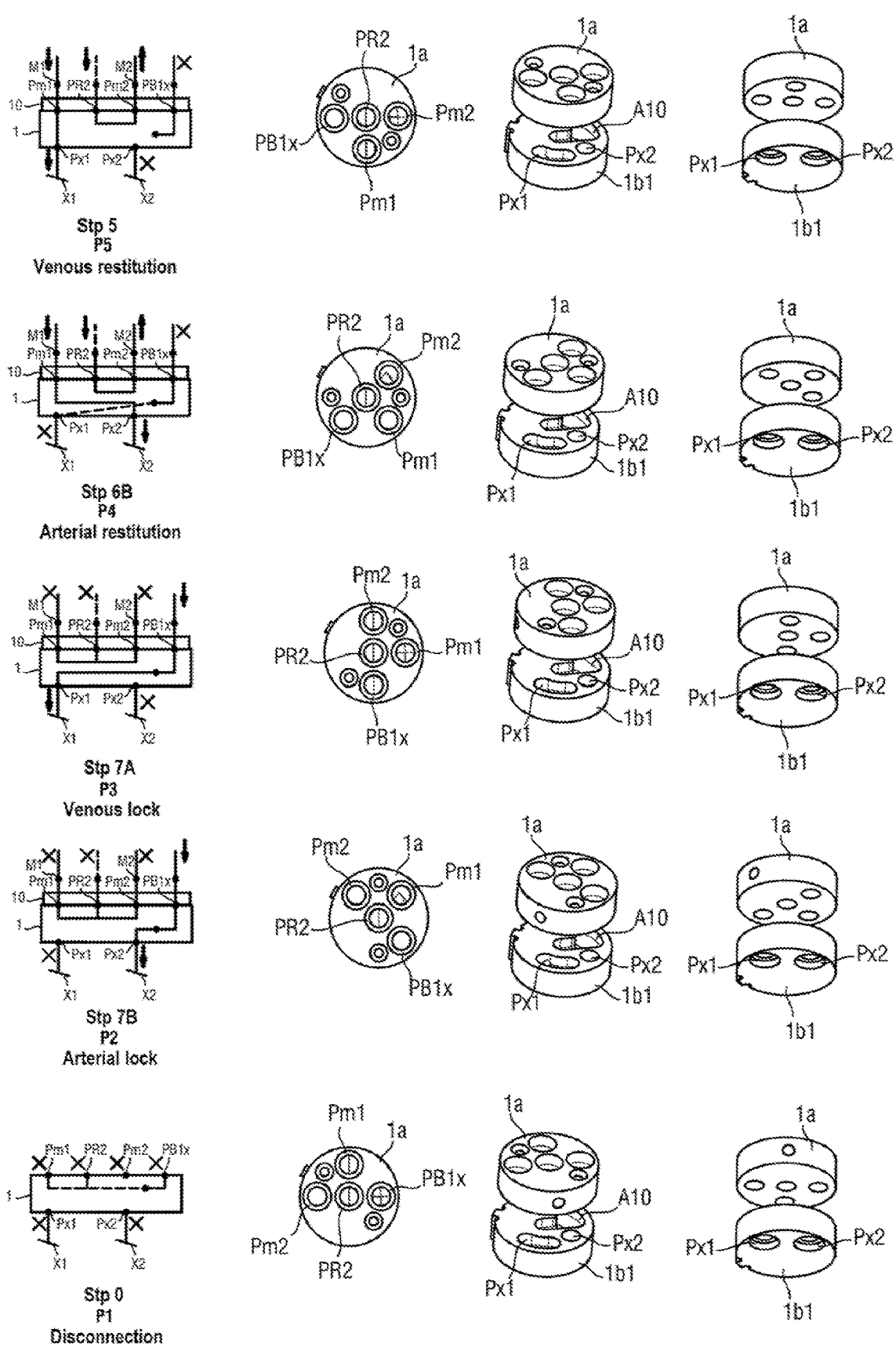
FIG. 9 shows an interface device 1 of the invention in a plurality of successive configurations, specifically the venous restitution configuration P5 (adopted in step Stp5, which is performed at the end of dialysis to restitute the blood and/or the dialyzate towards the patient via the venous tube X1 where it is possible to place a venous lock, this configuration P5 being adopted after the device 1 has been in its second configuration P6 in order to perform dialysis), the arterial restitution configuration P4 (adopted in step Stp6B that is performed to restitute the blood and/or the dialyzate towards the patient via the arterial tube X2 where it is possible to place the arterial lock, this configuration P4 being adopted after the device 1 has been in its second configuration P6 for performing dialysis and preferably after it has adopted the configuration P5 and performed venous restitution), followed by step Stp7A of putting the venous lock into place, which step is performed with the device 1 placed in the venous lock access configuration P3, followed by step Stp7B of putting the arterial lock into place, which step is performed with the device 1 placed in the arterial lock access configuration P2, followed by step Stp0 for disconnecting the connection means 10 and the external equipment 2 from the interface device 1, which device can remain permanently on the patient (either extracorporeally or in the form of a transcutaneous implant) remaining attached to the venous and arterial tubes X1 and X2.

As can be seen in FIGS. 8 and 9, the internal circuit A10 is formed inside the stator and opens out only facing the rotor 1a.

Thus, in the first configuration, the first port Pm1 can be put into communication with one or more other ports PR2, PB1x carried by the movable assembly in order to make it possible, where necessary, to degas at least some of the ports of the movable assembly and at least portions of the connection means 10, while isolating the arterial and venous tubes X2 and X1.

The interface device 2 is also adapted to adopt selectively an arterial lock access configuration P2 that is distinct from said first and second configurations P1 and P6 and from the venous lock access configuration P3.

Figure 1J:
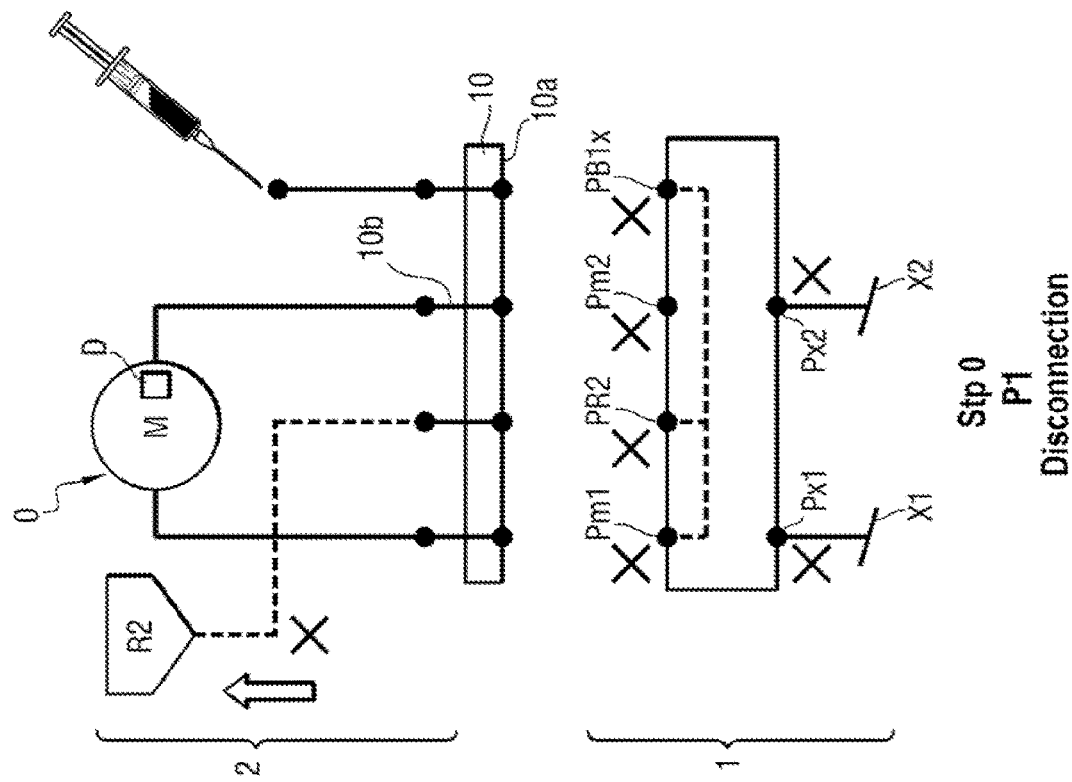
Figure 1I:
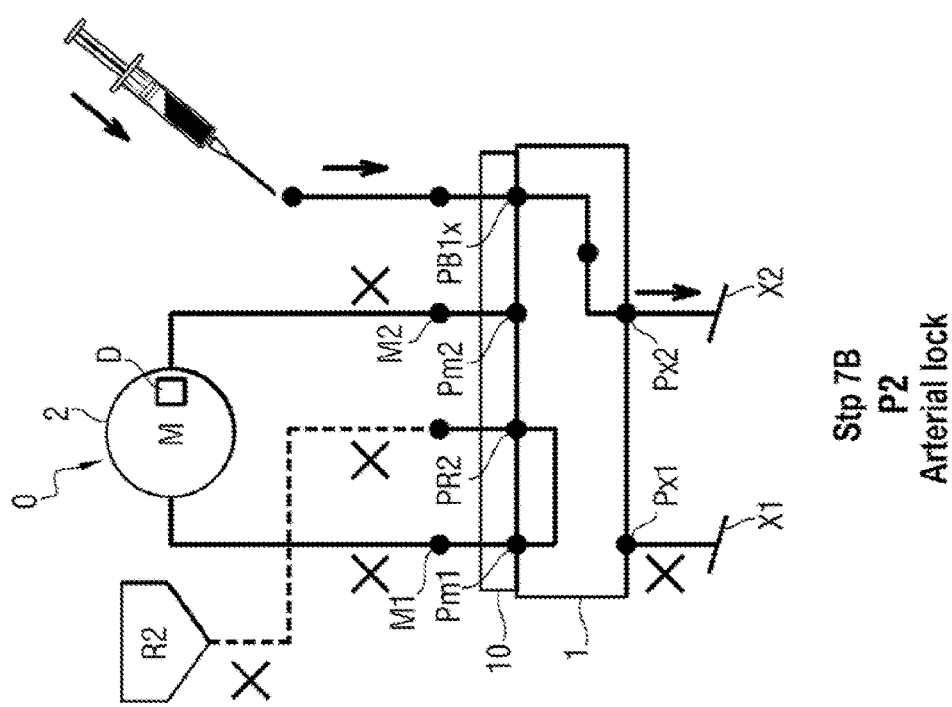

In this arterial lock access configuration P2 (adopted in step Stp3a as shown in FIGS. 1c, 1i), the third port Pb1x is connected to the arterial port Px2 while the first port Pm1 and the second port Pm2 are both isolated from the arterial port Px2, with the venous and arterial ports Px1 and Px2 then likewise being isolated from each other.

When ports are said to be isolated from one another or from each other, it should be understood that the ports are not in mutual fluid flow connection.

Acting via the third port Pb1x, this arterial lock access configuration P2 enables a locking fluid to be sucked from or injected into the arterial tube X2 for the purposes either of releasing the arterial tube and allowing blood to flow or liquid fluid to circulate, or else of locking the arterial tube X2 to oppose blood passing towards it.

A locking fluid is a substance having an anti-coagulating function and a buffer function to avoid blood passing into the tube containing it. Optionally, the locking fluid may have an antiseptic function.

Typically, after performing a hemodialysis, locking fluid is injected into each tube that is to remain in the patient until the next hemodialysis. The locking fluid serves to avoid the tube clogging and the need to replace it.

By means of the interface device 1, it is possible to inject the locking fluid into the venous tube X1 and/or to the arterial tube X2 or else to suck the locking fluid from it/them, while leaving this or these tube(s) connected to the interface device 1.

Once again, this reduces the need to handle couplings and ports and reduces the associated risks for the patient.

In order to suck the locking fluid coming from the venous tube X1 or from the arterial tube X2, the system of the invention may also include at least one locking fluid suction syringe B1x that is connected to the third port Pb1x via the interface means (10).

Figure 2:
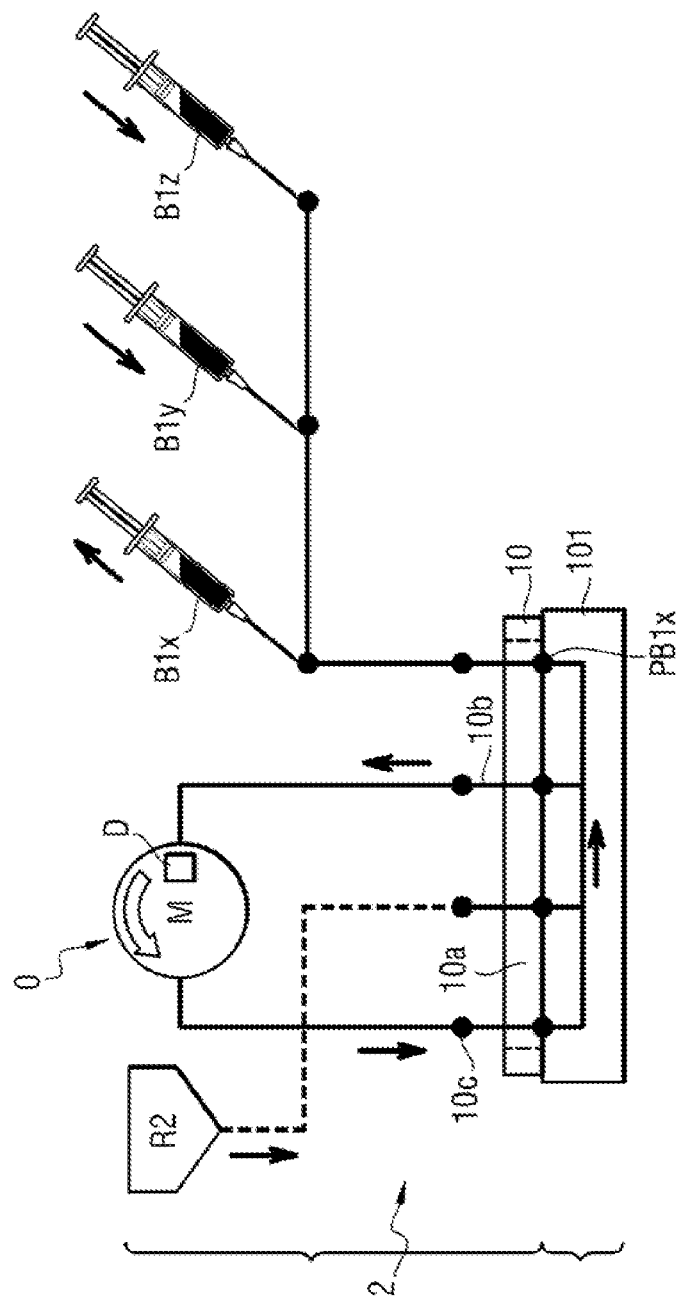
FIG. 2 shows the interface connection means 10 of the invention when connected to the external equipment 2 with a cap 101 fastened on the plug so as to put the flexible tubes 10b of the connection means into connection with one another via the internal volume of the cap (thus enabling the flexible tubes 10b to be filled with liquid fluid and gas to be expelled therefrom)

It should be observed that the port of the interface connection means 10 for connection to the third port Pb1x presents a flexible tube suitable for connecting to two couplings placed in parallel, as in FIG. 1a or to three couplings placed in parallel as in FIG. 2, each of these couplings being suitable for receiving a syringe such as a syringe B1x in order to suck the locking fluid, or a syringe B1z for injecting locking fluid to lock the tubes X1, X2, or else a syringe B1y for injecting physiological serum in order to rinse the tubes X1, X2.

In the embodiment shown in FIGS. 1a to 1j, it can be seen that the third port PB1x is designed to be connected either to the venous port Px1, or to the arterial port Px2, or possibly to a restitution port Pr2 for injecting a fluid to be restituted to the patient (e.g. a physiological serum or liquid medication). Thus, this single third port Px1 can be used with each of the venous or arterial ports Px1 or Px2 to insert a lock or to suck it out. To do this, the third port PB1x may be designed to be connected in turn with a locking fluid suction syringe B1x or with a locking fluid injection syringe B1z. Each syringe may be coupled manually by the hemodialysis practitioner.

This solution is also advantageous, since it makes it possible to perform locking operations on the venous or arterial ports using this single third port Pb1x.

In order to perform venous or arterial locking, it suffices to put the interface device in the venous or arterial lock access configuration and to inject an arterial or venous lock via that one of the ports Px1 or Px2 that is connected to the third port Pb1x.

The interface device of the invention thus makes it possible to perform the operations of removing or installing locking fluid in the venous tube X1 and the arterial tube X2 while leaving the hemodialysis machine 2 and the venous and arterial tubes X1 and X2 connected/attached to the ports in question of the interface device. Once again, this limits any risk of contaminating the circulatory system by connecting or disconnecting ports.

For this purpose, the system of the invention may include an arterial injection syringe B1z for injecting locking fluid that is connected to the third port Pb1x in order to be able to inject the locking fluid into the arterial tube X2.

In a preferred embodiment, the interface device also includes a restitution port Pr2 carried by said movable assembly 1a, and the interface device 1 is also adapted to adopt selectively a venous restitution configuration P5 (adopted in step Stp5) that is distinct from the other configurations P1, P6, P3 that can be adopted by the device.

In this venous restitution configuration P5, the restitution port Pr2 is connected to said second port Pm2 (specifically, this connection takes place via said internal circuit A10 formed in the stator and visible in FIGS. 4, 6, 8, 9) in order to be able to inject a restitution fluid into the hemodialysis machine 2, the first port Pm1 then being connected to said venous port Px1 and isolated from all of the other ports of the interface device, with the arterial port Px2 then being isolated at least from the venous port Px1, from the first port Pm1, and from the second port Pm2.

In this venous restitution configuration P5 (adopted in step Stp5 shown in FIGS. 1f, 9), the device 1 allows a fluid for restitution (a restitution fluid) to pass only to the second port Pm2 of the hemodialysis machine, while allowing the hemodialysis machine to inject fluid to the venous port X1 via the outlet port M1 that has been put into communication with the first port Pm1 and the venous port Px1.

For this purpose, the system of the invention may include apparatus R2 for feeding restitution fluid (e.g. a supply of physiological serum, a dialyzate, medication in liquid form) that is connected to the restitution port Pr2 via the connection means 10 in order to be able to inject the restitution fluid into the interface device 1 while it is in its venous restitution configuration P5, Stp5.

Since the hemodialysis machine 2 forms a circuit extending between its inlet port M2 and its outlet port M1, the hemodialysis machine pumps the restitution fluid from its inlet port M2 towards its outlet port M1 so as to pass the blood contained in the machine and restitute it to the venous tube X1 and then to the patient's circulatory system 3.

Thus, the volume of blood contained in the hemodialysis machine 2, in the venous tube X1, and in the pipes connecting the hemodialysis machine 2 to the interface device 1 can be restituted to the patient. This is particularly important in order to limit the quantity of blood lost by the patient during hemodialysis.

In a preferred embodiment, the device 1 is also adapted to adopt selectively an arterial restitution configuration P4 in step Stp6B that is distinct from the other configurations P1, P6, P2, P3, P5 that can be adopted by the interface device.

In this arterial restitution configuration P4 (see step Stp6B in FIGS. 1g and 9), the restitution port Pr2 is connected to said second port Pm2 (specifically, this connection takes place via said internal circuit A10 formed in the stator) in order to be able to inject restitution fluid to the external equipment 2, the first port Pm1 then being connected to said arterial port Px2 and being isolated from all of the other ports of the interface device, and the venous port Px1 being isolated at least from the arterial port Px2, the first port of Pm1, and the second port Pm2.

In this arterial restitution configuration P4 in step Stp6B, the restitution fluid passes from the restitution port Pr2 to the second port Pm2, and then passes via the machine M and its debubbler D to leave it and pass through the first port Pm1 to the arterial port Px2 (the interface device 1 in the arterial restitution configuration connects together it supports Pm1 and Px2, isolating them from the other ports of the interface device).

In an embodiment that is not shown, it is also possible in the restitution configuration for both the venous and the arterial ports to be connected to the restitution port Pr2 or possibly to the first port Pm1 in order to perform restitution simultaneously. This solution provides a saving in time during restitution, but it presents the drawback of not controlling the volume of fluid that is restituted to each tube X1 and X2.

As mentioned above, the restitution fluid may be physiological serum.

In this arterial restitution configuration P4, the arterial tube X2 is filled with restitution fluid, and the blood present in the tube X2 is pushed towards the circulatory system 3.

This restitution of blood limits the loss of blood during hemodialysis and avoids the risk of the arterial tube X2 clogging.

In a particular embodiment, the interface device may be adapted so that when it is in its first configuration P1 (step Stp0 and/or step Stp1), its restitution port Pr2 is then connected to at least one of said first and second ports Pm1 and Pm2.

Thus, the first and second ports Pm1 and Pm2 can be degassed by injecting a (liquid) fluid via the restitution port Pr2.

In a particular embodiment, the interface device 1 may include a motordriven control mechanism (not shown) for moving the movable assembly 1a relative to the stator 1b, thereby causing the device 1 to go from one of its configurations to another of its configurations in a predefined succession of configurations.

For example, the control mechanism may either act directly on the movable assembly, or else it may act indirectly by moving the plug 10.

In other words, the control mechanism serves to cause the device to switch from a current configuration in which it is to be found to a selected other configuration of the device, with said other configuration being selected from the various different configurations that the device can adopt selectively.

The sequencing of the various configurations needed to perform hemodialysis completely is described in detail below.

As mentioned above, the connection between the machine 2 and the interface device takes place via interface connection means 10 including a plug 10a and a plurality of flexible tubes 10b, each having one end connected to the plug 10a and another end carrying at least one connection coupling 10c (each connection coupling is carried by a single one of the flexible tubes of the connection means to which it corresponds, where such a connection coupling may be male or female, e.g. a coupling of the Luer standard).

Each given connection coupling 10c is for establishing fluid flow connection between the tube carrying the given coupling 10c and one of said ports of the external equipment 2 that corresponds to said given connection coupling 10c.

The plug 10a is arranged to be connected mechanically in releasable manner to said interface device 1 in such a manner that when the plug 10a is mechanically connected to said interface device 1, each of the flexible tubes 10b of the plurality of flexible tubes is in fluid flow connection with a corresponding single one of the ports carried by said movable assembly 1a.

The connection couplings 10c can be moved relative to one another within the limits of the freedom made possible by the flexible tubes 10b.

The plug 10a of the connection means 10 and the movable assembly 1a of the interface device 1 are shaped so that when the plug 10a is mechanically connected to said interface device 1, the plug (10a) is constrained to move together with the movable assembly/rotor 1a when the rotor 1a moves relative to the stator 1b.

Thus, when the plug 10a is mechanically connected to said interface device 1, the user can move the plug 10a relative to the stator 1b, thereby causing the movable assembly 1a to move relative to the stator 1b in order to cause the interface device 1 to switch from one of its configurations to another one of its configurations.

To enable the plug 10a to be constrained to move together with the movable assembly 1a, two pins 10d are carried by the plug 10a and two recesses 1a1 that are complementary to the pins 10d are made in said movable assembly 1a.

These pins 10d and recesses 1a1 are designed so that the plug 10a can be assembled on the movable assembly 1a with the plug 10a oriented in only one position relative to the movable assembly 1a. Thus, the pins 10d and the recesses 1a1 form keying means.

Preferably, the pins 10d are of sufficient length to enable each of the pins 10d to penetrate into the corresponding one of the recesses 1a1, while the remainder of the plug 10a is held at a distance from the interface device 1. Thus, the pins 10d facilitate pre-positioning and guidance of the plug 10a relative to the movable assembly while the plug is being moved towards the interface device 1 in order to connect the plug 10a mechanically to the interface device 1.

The interface connection means 10 also include an indicator 10e for indicating the position of the plug 10a, which indicator is visible from outside the interface connection means 10 so as to inform an operator about the current position of the plug relative to the stator 1b when the plug 10a is mechanically connected to said interface device 1. Specifically, and as shown in FIGS. 1a, 1b, 3, 5, 6, the indicator 10e is formed by a pointer extending radially relative to a longitudinal axis of the plug.

The pointer is accessible from outside the interface assembly 100 so as to enable the operator to manipulate the pointer and thereby move the plug 10a relative to the stator when the plug is mechanically connected to said interface device 1.

Preferably, the interface connection means 10 include at least one mechanical latch 10f arranged:
to prevent the plug 10a and the interface device 1 from moving apart when the plug 10a is mechanically connected to said interface device 1 and while the plug 10a is not in a predetermined position relative to the stator 1b; and
to allow the plug 10a and the interface device 1 to move apart when the plug 10a is mechanically connected to said interface device 1 and while the plug 10a is in said predetermined position relative to the stator 1b.

Thus, this at least one latch 10f allows the plug 10a and the interface device 1 to be coupled together mechanically and to be uncoupled only when the plug 10a is in a predetermined position relative to the stator 1b.

Since the position of the plug 10a relative to the movable assembly 1a is determined (e.g. by the pins 10d) and since the position of the movable assembly relative to the stator 1b determines the current configuration adopted by the interface device 1, allowing the plug 10a and the interface device 1 to be coupled or uncoupled only when the plug is in a predetermined position relative to the stator serves to guarantee that such coupling or uncoupling always takes place while the interface device 1 is in a predefined given configuration.

Specifically, said at least one mechanical latch 10f is arranged to allow the plug 10a and the interface device 1 to move apart only when the interface device 1 is in its first configuration P1; Stp1, with the flow of fluid between the ports Pm1, PR2, Pm2, PB1x and each of the venous and arterial ports Px1 and Px2 then being prevented.

Thus, the plug 10a can be connected or disconnected only when the venous and arterial ports Px1 and Px2 are secured to prevent any flow of fluid via the venous and arterial tubes X1 and X2.

Figure 3:
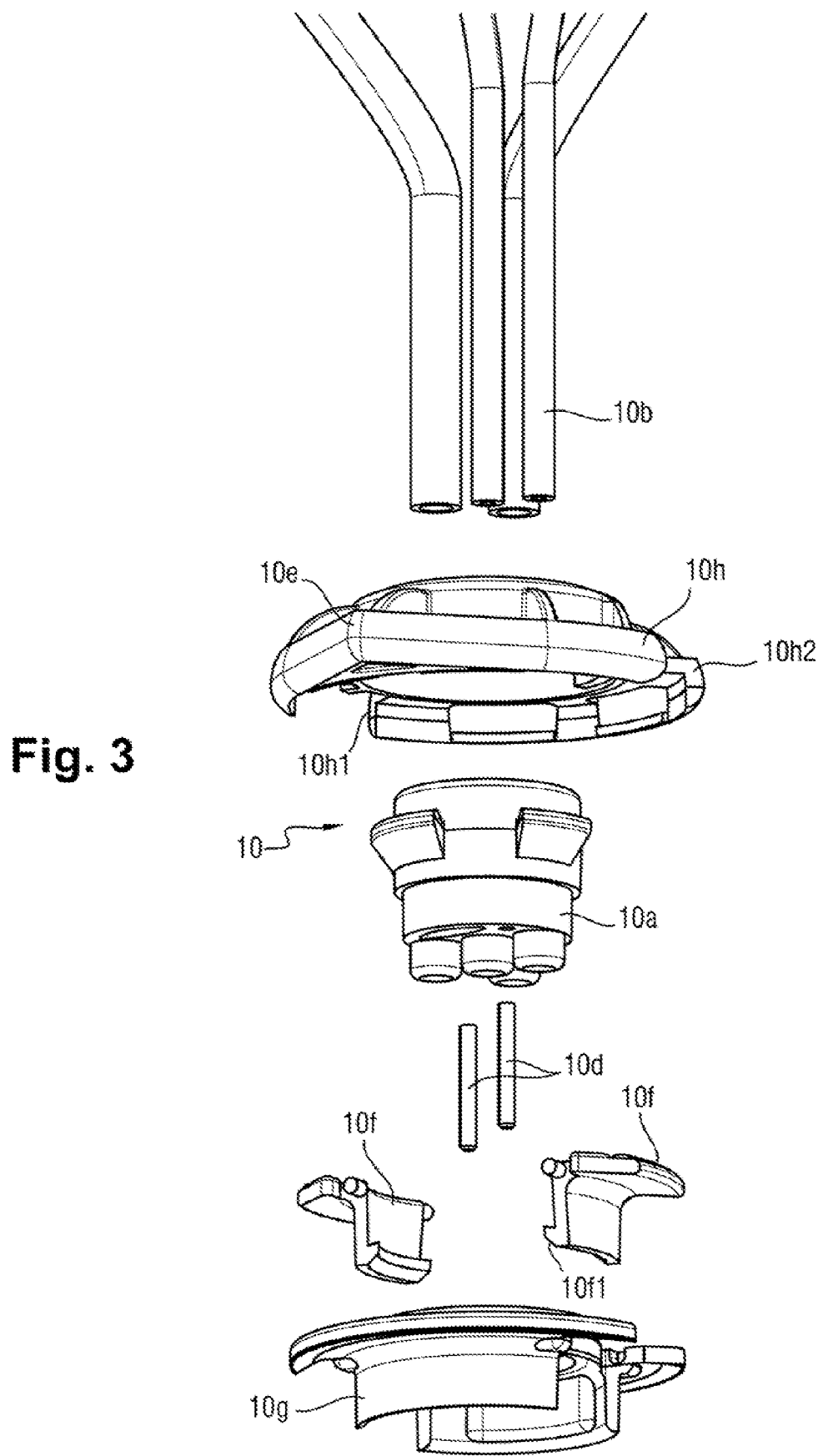
FIG. 3 shows an exploded view of the interface connection means 10 of the invention.
Figure 4:
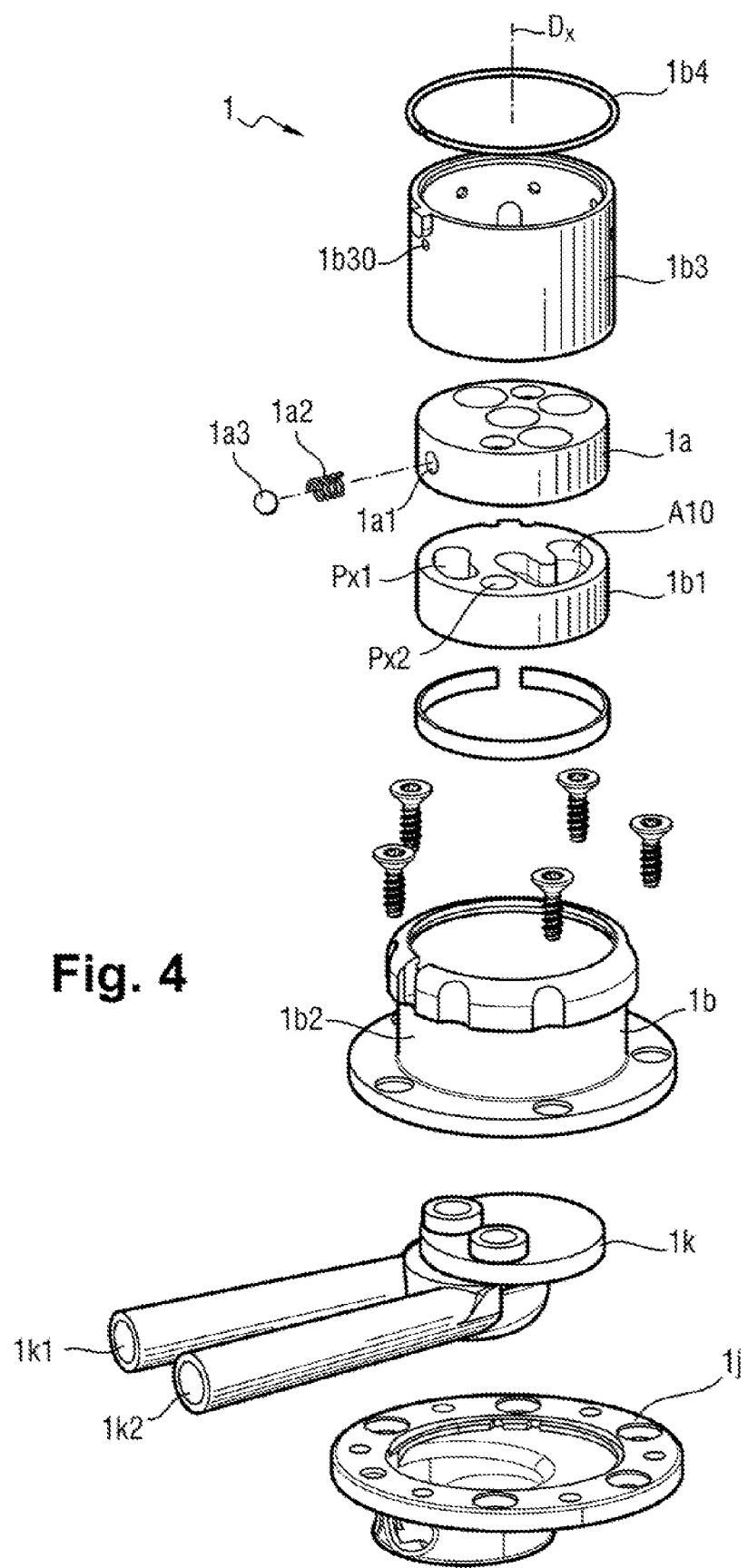
FIG. 4 shows an exploded view of the interface device 1 in a particular embodiment of the invention (specifically, the device possesses a base that is arranged to be fastened on a bone of the patient)
Figure 5:
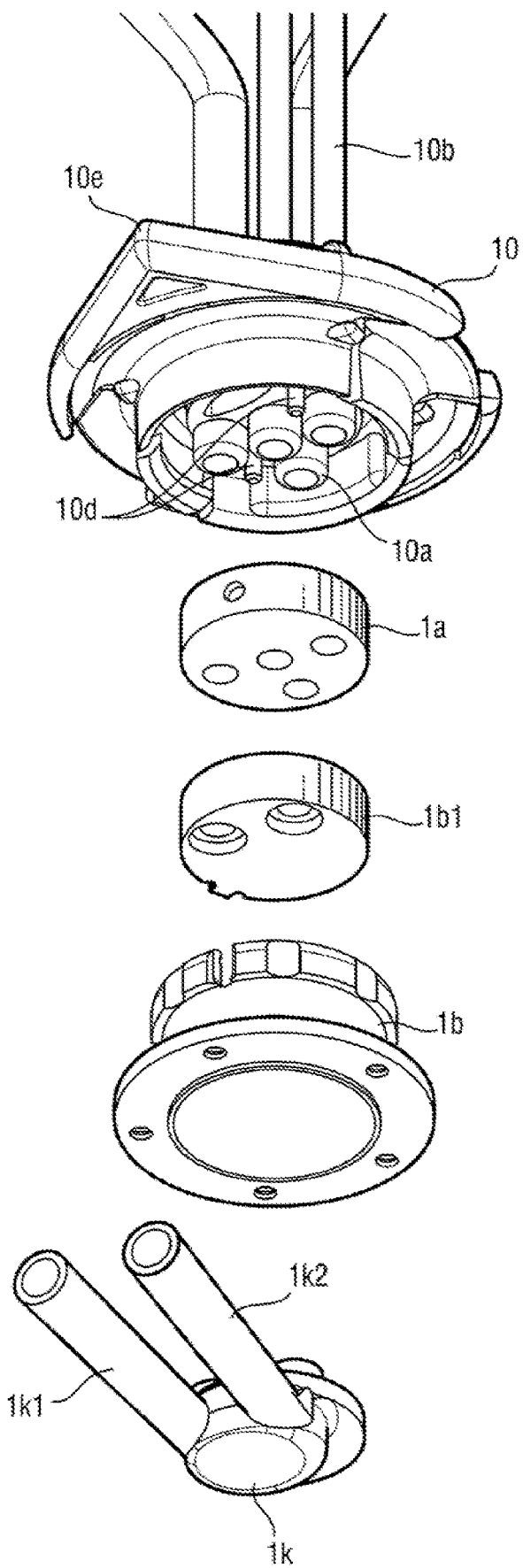
FIG. 5 shows a first exploded view of an interface assembly 100 of the invention comprising the interface device 1 and the interface connection means 10.

As can be understood from FIG. 3, which shows the interface connection means 10, the interface connection means include a connection disk 10g surrounding the plug 10a.

The connection disk 10g is shaped:
firstly to be constrained to turn with the stator 1b when the plug 10a is mechanically connected to said interface device 1; and
secondly to allow the connection disk 10g to turn relative to the plug 10a that extends inside the connection disk 10g.

The latch comprises two arms 10f arranged on either side of the connection disk 10g and mounted to pivot relative to the connection disk 10g that surrounds the plug 10a.

Each of these arms presents a respective catch 10f1 at one of its ends, each catch being arranged to penetrate into an annular groove 1b2 formed in the stator 1b when the plug 10a is mechanically connected to said interface device 1.

While positioned in the annular groove 1b2, each of the catches 10f1 opposes the plug 10a moving away from the interface device 1.

Thus, in order to allow the plug 10a to be moved away from the interface device 1, it is necessary to begin by moving the catches 10f1 out of the annular groove 1b2, and to do this it is necessary to cause the arms 10f to pivot relative to the connection disk 10g.

As can be understood from FIGS. 1a, 1b, and 3, the interface connection means 10 include an indicator ring 10h carrying said pointer 10e.

The indicator ring 10h is mechanically secured to the plug 10a so that it turns with the plug 10a during movement of the plug 10a relative to the stator 1b.

The indicator ring 10h includes two cutouts 10h1 and 10h2, each giving access to a respective one of the arms 10f when the plug 10a is in a first predetermined angular position relative to the connection disk 10g carrying the arms 10f.

The indicator ring 10h is arranged to prevent the arms 10f from pivoting relative to the connection disk 10g whenever the indicator ring 10h is in an angular position (relative to the connection disk 10g) other than said first predetermined angular position relative to the connection disk 10g.

Thus, coupling between the plug and the interface device 1 is possible only if:
if firstly the plug 10a is in a predetermined angular position relative to the movable assembly 1a; and
if secondly the arms 10f are free to pivot relative to the connection disk 10g, i.e. if the plug 10a and the indicator ring 10h are in said first predetermined angular position relative to the connection disk 10g.

Preferably, the plug 10a presents a plurality of male ports, each oriented to penetrate into a corresponding respective one of the ports Pm1, PR2, Pm2, PB1x carried by the movable assembly 1*a*, thereby establishing a plurality of fluid flow connections between the male ports carried by the plug 10*a* and the corresponding ports carried by the movable assembly 1*a*.

Preferably, said plug 10*a* and said flexible tubes are made out of polymer materials, while at least one of the movable assembly 1*a* and the stator 1*b* is made at least in part out of a metal material.

Using polymer materials makes it possible to obtain removable interface connection means 10 at a cost that is low compared with the cost of the interface device 1 presenting at least one part made out of metal that is stronger and consequently more expensive.

The metal material may be selected from a stainless-steel alloy, a titanium alloy, or some other biocompatible metal alloy.

Thus, the interface connection means 10 may be designed for single use (the connection means 10 then being a consumable), while the interface device 1 is designed for multiple use.

It should be observed that the stator of the interface device 1 may present a metal base 1*j* that is designed to be implanted on a bone of the patient and to remain there permanently.

As shown in FIGS. 4, 5, 6, and 7, such a metal base 1*j* may present holes for passing screws to secure the base 1*j* on a patient's bone by screw fastening.

As can be understood from these FIGS. 4 to 7, the stator of the interface device 1 may also present an insert 1*k* designed to define first and second fluid-passing channels 1*k*1 and 1*k*2, each having a bend.

The first of these channels 1*k*1 presents a first end opening out facing a first passage made through a disk 1*b*1 of the stator 1*b* that is to be found in an internal enclosure 1*b*3 of the stator 1*b* so as to form said venous port Px1 of the interface device 1.

The second of these channels 1*k*2 presents a first end opening out facing a second passage made through a disk 1*b*1 of the stator 1*b* so as to form said arterial port Px2 of the interface device 1.

The first of these channels 1*k*1 presents a second end that is designed to be put into fluid flow connection in series with the venous tube X1, this connection possibly being made by a first specific coupling 1*k*10 so as to be reversible.

Likewise, the second of these channels 1*k*2 presents a second end that is designed to be put into fluid flow connection in series with the arterial tube X2, this connection possibly being made by a second specific coupling 1*k*20 so as to be reversible.

Each of the channels 1*k*1 and 1*k*2 of the insert 1*k* has a bend to enable the venous and arterial tubes X1 and X2 to extend longitudinally in a plane perpendicular to a direction Dx along which the ports carried by the movable assembly 1*a* extend. This produces a device that is more compact, in which the stator can be placed against the patient with the venous and arterial tubes X1 and X2 running along the outer surface of the patient while the ports carried by the movable assembly 1*a* extend perpendicularly to that outer surface.

This makes it easier to connect the interface connection means 10 to the interface device 1 that remains permanently on the patient. A cover (not shown) is put into place on the interface device 1 so as to protect it between two sessions (the ports for connection to the external equipment 2 are masked in sealed manner by the cover).

As shown in FIGS. 4 to 7, the movable assembly 1*a* is preferably a rotor 1*a* in the form of a disk rotatably mounted inside said internal enclosure 1*b*3 of the stator 1*b*, which presents a cylindrical internal bore.

A mechanism for indexing turning of the rotor relative to the internal enclosure 1*b*3 is provided in the form of a spring placed in a radial blind bore 1*a*1 of the rotor, of a spring 1*a*2 placed in the bore 1*a*1, and of a ball 1*a*3 urged by the spring against a cylindrical inside annular face of the internal enclosure 1*b*3.

The internal enclosure 1*b*3 is provided with a plurality of radial perforations 1*b*30 of diameter smaller than the diameter of the ball and that lie on the path followed by the ball 1*a*3 while the rotor is turning.

Turning of the rotor 1*a* relative to the stator 1*b* is thus indexed each time the ball penetrates into one of the perforations 1*b*30. Each indexed position of the rotor corresponds to a single one of said configurations that can be adopted by the interface device 1.

The stator 1*b* includes a disk 1*b*1 placed inside said internal enclosure 1*b*3 of the stator 1*b*.

The disk of the rotor 1*a* includes a surface that is to be pressed against a complementary surface forming part of the stator disk 1*b*1 so as to provide these surfaces with sealing against any leak of fluid along these surfaces of the disks.

In order to enable the disk 1*b*1 of the stator 1*b* to be pressed against the disk of the rotor 1*a*, said internal enclosure 1*b*3 of the stator 1*b* includes an axial abutment 1*b*4, specifically a resilient ring 1*b*4, against which the disk of the rotor 1*a* comes to bear.

On one side, the stator disk 1*b*1 bears against the disk of the rotor 1*a*, and on its other side it bears against the insert 1*k* that defines the first and second fluid-passing channels 1*k*1 and 1*k*2.

In this example, the rotor and stator disks are pressed against each other by the insert 1*k*, which is made of an elastically compressible material such as silicone or latex.

Thus, the stator and rotor disks form a disk stack compressed between the resilient ring 1*b*4 and the insert Such an assembly is advantageous, since by removing the resilient ring 1*b*4 from the internal enclosure 1*b*3, it is possible to unstack the stator disk 1*b*1 and the disk of the rotor 1*a* to perform maintenance on the interface device 1, and possibly to replace the disks.

There follows a description of the operation of the assembly 100 of the invention.

FIG. 2 shows a preparatory step in which the interface connection means 10 are provided with a cap 101 assembled on the plug 10*a* to define a closed space into which each of the flexible tubes 10*b* of the connection means opens out. This space enables the flexible tubes 10*b* to be put into communication with one another.

The coupling means 10*c* of these connection means are in fluid flow connection with the ports of the external equipment 2, i.e. of the machine 2, of the apparatus R2 (for supplying liquid such as physiological serum), and of the syringe(s) B1*x*, B1*y*, B1*z*.

The pump of the machine 2 is put into operation, thereby causing liquid to flow around a loop between the machine 2 and the interface connection means 10, passing via the debubbler D that serves to remove bubbles from the liquid.

The machine 2 continues to circulate the liquid until it, or an operator, detects that the circuit of the machine and the interface device contains liquid only.

By way of example, the liquid is physiological serum.

After this preparatory step shown in FIG. 2, the operation of the pump of the machine is stopped, the flexible tubes are optionally clamped, the cap 101 is removed, and a first step (Stp1 shown in FIG. 1*b*) is performed that consists in mechanically connecting the ports of the plug 10a to the ports of the interface device 1, which is in its first configuration.

In this example, the venous and arterial tubes X1 and X2 are already connected to the corresponding ports Px1 and Px2 of the interface device 1.

Thus, the ports of the external assembly 2 are connected to the interface device via the interface connection means 10.

The apparatus R2 that is connected to the port PR2 maybe a specific port of the hemodialysis machine 2 that is used solely while restituting blood at the end of hemodialysis, or possibly it may be a pouch of fluid or of medication for being injected at the end of hemodialysis.

The interface device 1 is then caused to switch into the arterial lock access configuration P2 (step Stp3a shown in FIG. 1c).

The suction syringe B1x is then actuated. The locking fluid contained in the arterial tube X2 is then sucked out.

Actuation of the syringe(s) may be motor-driven and controlled by the control unit of the external equipment.

After sucking out the arterial lock, the pump of the external equipment 2 is put into operation and the small amount of gas contained in the interface device is then discharged to the debubbler. The connection means 10 and the interface device 1 are now entirely full of liquid.

The interface device 1 is then caused to switch into the venous lock access configuration P3 (step Stp3b shown in FIG. 1d).

The suction syringe B1x or another syringe is then actuated. The locking fluid contained in the venous tube X1 is then sucked out.

Once the tubes X1 and X2 are free of the locking fluid, the interface devices caused to switch into its second configuration P6 (step Stp4). In this second configuration P6, the arterial tube X2 is put into communication with the inlet port M2 via the port Pm2, and the venous tube X1 is put into communication with the outlet port M1. The patient's blood can then circulate in a loop via the hemodialysis machine 2 in order to be dialyzed therein. The small amount of gas contained in the interface device is sucked out and discharged by the debubbler D.

Once hemodialysis has been performed, and in optional manner, it may be desired to restitute a particular liquid to the patient. Under such circumstances, this liquid may be conveyed via a restitution port PR2 that forms part of the interface device. This port Pr2 may be connected to a specific blood outlet R2 of the hemodialysis machine or to a pouch R2 containing blood or medication.

For this purpose, the control mechanism is actuated so that the interface device switches into the venous restitution configuration P5 (step Stp5 shown in FIG. 1f). In this configuration P5, the port PR2 is put into communication with the port Pm2, and the venous tube X1 is put into communication with the outlet port M1. The restitution liquid then flows from the apparatus R2 to the venous tube X1 passing successively via a first one of the tubes of the connection means 10, via the port Pr2, via the port Pm2, via a second one of the tubes of the connection means 10, via the inlet port M2, via the hemodialysis machine 2, via the outlet port M1, via a third one of the tubes of the connection means 10, via the port Pm1, via the port Px1, and finally it reaches the venous tube X1.

Once this step Stp5 has finished, the interface device 1 is then caused to switch into the arterial restitution configuration P4 (step 6B shown in FIG. 1g), which allows:

the arterial port Px2 and/or the arterial tube X2 to be closed (possibly with a connection to the port PB1x); and the peripheral apparatus R2 to be put into communication with the machine inlet port M2 via the restitution port PR2 and via the second port Pm2.

A detector device may detect the arrival of the physiological serum and thus detect the end of the arterial restitution operation.

The restitution operation comes to an end when a predetermined volume of liquid has been restituted to the arterial tube X2.

Once this step 6B has terminated, the interface device 1 is caused to switch into the venous lock access configuration P3 (step Stp7A shown in FIG. 1h), which serves firstly to allow the syringe B1z to be put into communication with the venous tube X1 via the port PB1x and the port Px1.

In this locking configuration, the port Px2 is closed.

The locking fluid leaves the injection syringe B1z and goes to the venous tube X1.

Once this step 7A has terminated, the interface device 1 is caused to switch into the arterial lock access configuration P2 (step Stp7B shown in FIG. 1i), which serves firstly to allow the syringe B1z to be put into communication with the arterial tube X2 via the port PB1x and the port Px2.

In this arterial lock access configuration P2, the port Px2 is closed.

The locking fluid leaves the injection syringe B1z and goes to the arterial tube X2.

After injecting the locks in this way, the connection means 10 may be separated from the interface device 1, the interface device then being in its first configuration P1 as shown in step Stp0 of FIG. 1j.

The interface device 1 of the invention is particularly easy to use since it is switched from any of its configurations to any other of its configurations merely by moving the movable assembly 1a relative to the stator 1b.

The invention claimed is:
1. An interface device between external equipment and at least a venous tube for connecting to a patient system in order to transfer fluid from the equipment to the patient system, the interface device comprising at least:
 a first port adapted to be connected to an outlet port of the external equipment; and
 a venous port for injecting the fluid into the venous tube;
 the interface device being adapted to adopt selectively a first configuration in which fluid is prevented from passing between the first port and the venous port and a second configuration in which the first port is connected to the venous port to allow fluid to pass from the first port to the venous port, the interface device being characterized in that:
 it includes a third port and is adapted to adopt selectively a venous lock access configuration that is different from said first and second configurations the third port being connected in this venous lock access configuration to the venous port while the first port is isolated from the venous port; and in that
 the venous port is carried by a stator of the interface device, the first port and the third port being carried by a movable assembly of the interface device that is movable relative to the stator, the interface device being arranged to pass from any one of its configurations to another one of its configurations by the movable assembly moving relative to the stator.

2. An interface device according to claim 1, wherein the movable assembly is a rotor mounted to turn relative to said stator.

3. An interface device according to claim 1, wherein the movable assembly has a face that is visible from the outside of the interface device, and each of the ports carried by the movable assembly opens out in said face.

4. An interface device according to claim 3, wherein said face of the movable assembly and the ports carried by that movable assembly are located completely inside a recess of the stator.

5. An interface device according to claim 1, wherein the ports carried by the movable assembly are female ports that open out in a direction that is common to these female ports.

6. An interface device according to claim 1, also including a second port carried by said movable assembly of the interface device, the interface device further being adapted so that in said venous lock access configuration the first port and the second port are both isolated from the venous port.

7. An interface device according to claim 6, adapted to form an interface between the external equipment, which comprises a hemodialysis machine, and an arterial tube for connecting to said patient system in order to transfer fluid from the patient system to the hemodialysis machine, said second port being adapted to be connected to an inlet port of the hemodialysis machine, the interface device also including an arterial port carried by the stator to receive patient fluid coming from the arterial tube;

the interface device further being adapted to prevent fluid from passing between the second port and the arterial port when the device is in its first configuration and to allow fluid to pass between the second port and the arterial port when the device is in its second configuration.

8. An interface device according to claim 1, further adapted to put the first port into communication via an internal circuit of the interface device with at least one other one of the ports carried by the movable assembly when the interface device is in its first configuration, and to prevent communication via the internal circuit between the first port and the other ports carried by the movable assembly when the interface device is in its second configuration.

9. An interface device according to claim 1, adapted to adopt selectively an arterial lock access configuration that is distinct from said first and second configurations and from the venous lock access configuration, in this arterial lock access configuration the third port being connected only to the arterial port while the first port and the second port are both isolated from the arterial port, the venous and arterial ports then also being isolated from each other.

10. An interface device according to claim 1, also including a restitution port carried by said movable assembly, the interface device being adapted to adopt selectively a venous restitution configuration distinct from the other configurations of the device, the restitution port being connected in this venous restitution configuration to said second port in order to be able to inject a restitution fluid into the external equipment, which comprises a hemodialysis machine, the first port then being connected to said venous support and being isolated from all of the other ports of the interface device, and the arterial port being isolated at least from the venous port, from the first port, and from the second port.

11. An interface device according to claim 10, wherein the interface device is adapted to adopt selectively an arterial restitution configuration that is distinct from the other configurations of the device, the restitution port being connected in this arterial restitution configuration to said second port in order to be able to inject a restitution fluid into the external equipment, which comprises a hemodialysis machine, the first port then being connected to said arterial port and being isolated from all of the other ports of the interface device, and the venous port being isolated at least from the arterial port, from the first port, and from the second port.

12. An interface device according to claim 10, wherein the interface device is adapted so that when it is in its first configuration, its restitution port is then connected to at least one of said first and second ports.

13. An interface device according to claim 1, wherein the interface device includes a motordriven control mechanism and is arranged for moving the movable assembly relative to the stator, thereby causing the device to go from one of its configurations to another of its configurations.

14. An interface assembly comprising an interface device according to claim 1 and interface connection means comprising a plug and a plurality of flexible tubes, each having one end connected to the plug and another end carrying at least one connection coupling, each given connection coupling being for establishing a fluid flow connection between the flexible tube carrying the given connection coupling and a corresponding one of said ports of the external equipment, the plug being arranged to be mechanically connected in releasable manner to said interface device in such a manner that when the plug is mechanically connected to said interface device, each of the flexible tubes of the plurality of flexible tubes is in fluid flow connection with only one of the ports carried by said movable assembly that corresponds thereto.

15. An interface assembly according to claim 14, wherein the plug and the movable assembly of the interface device are shaped so that when the plug is mechanically connected to said interface device, the plug is constrained to move together with the movable assembly when the movable assembly moves relative to the stator.

16. An interface assembly according to claim 15, wherein the interface connection means include an indicator for indicating the position of the plug, which indicator is visible from outside the interface connection means so as to inform an operator about the current position of the plug relative to the stator when the plug is mechanically connected to said interface device.

17. An interface assembly according to claim 14, wherein the interface connection means include at least one mechanical latch arranged:

to prevent the plug and the interface device from moving apart when the plug is mechanically connected to said interface device and while the plug is not in a predetermined position relative to the stator; and to allow the plug and the interface device to move apart when the plug is mechanically connected to said interface device and the plug is in said predetermined position relative to the stator.

18. An interface assembly according to claim 14, wherein the plug presents a plurality of male ports, each oriented to penetrate into a corresponding respective one of the ports carried by the movable assembly, thereby establishing a plurality of fluid flow connections between the male ports carried by the plug and the corresponding ports carried by the movable assembly.

19. An interface assembly according to claim 14, wherein said plug and said flexible tubes are made out of polymer materials, while at least one of the movable assembly and the stator is made at least in part out of a metal material.

20. A hemodialysis system comprising an interface assembly according to claim 14, comprising:

a second port carried by said movable assembly of the interface device, the interface device further being adapted so that in said venous lock access configuration the first port and the second port are both isolated from the venous, and external equipment that comprises a hemodialysis machine, the first port of the interface device being releasably connected to the outlet port of the hemodialysis machine via the interface connection means and the second port of the interface device being releasably connected to the inlet port of the hemodialysis machine via the interface connection means, the hemodialysis machine including a pump arranged to cause fluid to flow from its inlet port to its outlet port, the hemodialysis machine also comprising a venous tube and an arterial tube, the venous tube being connected to the venous port of the interface device. the venous tube being for connection to a patient circulatory system in order to transfer blood via the interface device and via the interface connection means from the hemodialysis machine to the circulatory system, the arterial tube being connected to the arterial port of the interface device, the arterial tube being for connecting to said patient circulatory system in order to transfer blood via the interface device and via the interface connection means from the circulatory system to the hemodialysis machine.

21. A hemodialysis system according to claim 20, wherein the system includes a locking fluid suction syringe connected to the third port via the interface connection means so as to be able to suck locking fluid coming from the arterial tube.

* * * * *